US010590199B2

(12) United States Patent
Belk et al.

(10) Patent No.: US 10,590,199 B2
(45) Date of Patent: Mar. 17, 2020

(54) PD-L1-SPECIFIC ANTIBODIES AND METHODS OF USING THE SAME

(71) Applicant: Checkpoint Therapeutics, Inc., New York, NY (US)

(72) Inventors: Jonathan Belk, Lebanon, NH (US); Nathan J. Sharkey, Lebanon, NH (US); Leonid Gorelik, Newton, MA (US)

(73) Assignee: CHECKPOINT THERAPEUTICS, INC., New York, NY (US)

( * ) Notice: Subject to any disclaimer, the term of this patent is extended or adjusted under 35 U.S.C. 154(b) by 337 days.

(21) Appl. No.: 15/636,610

(22) Filed: Jun. 28, 2017

(65) Prior Publication Data

US 2018/0002424 A1 Jan. 4, 2018

Related U.S. Application Data

(60) Provisional application No. 62/356,105, filed on Jun. 29, 2016.

(51) Int. Cl.
| | | |
|---|---|---|
| *C07K 16/28* | (2006.01) | |
| *A61K 39/395* | (2006.01) | |
| *A61P 35/00* | (2006.01) | |
| *A61K 45/06* | (2006.01) | |
| *C07K 16/30* | (2006.01) | |

(52) U.S. Cl.
CPC ...... *C07K 16/2827* (2013.01); *A61K 39/3955* (2013.01); *A61K 45/06* (2013.01); *A61P 35/00* (2018.01); *C07K 16/30* (2013.01); *C07K 2317/56* (2013.01); *C07K 2317/565* (2013.01); *C07K 2317/567* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,175,082 B2 | 11/2015 | Zhou et al. | |
| 2003/0118592 A1 | 6/2003 | Ledbetter et al. | |
| 2003/0133939 A1 | 7/2003 | Ledbetter et al. | |
| 2010/0047245 A1 | 2/2010 | Lacey et al. | |
| 2013/0323249 A1 | 12/2013 | Zhou et al. | |
| 2015/0274835 A1* | 10/2015 | Marasco | C07K 16/3076 424/142.1 |
| 2015/0344573 A1 | 12/2015 | Chang et al. | |
| 2016/0311903 A1* | 10/2016 | West | A61K 49/0021 |
| 2017/0198050 A1* | 7/2017 | Eckelman | C07K 16/2827 |
| 2018/0118836 A1* | 5/2018 | Bernett | C07K 16/2863 |

FOREIGN PATENT DOCUMENTS

| | | |
|---|---|---|
| WO | WO 2007/053718 A1 | 5/2007 |
| WO | WO 2011/021009 A1 | 2/2011 |
| WO | WO 2014/055897 A2 | 4/2014 |
| WO | WO 2016/100985 A2 | 6/2016 |

OTHER PUBLICATIONS

Van Regenmortel MHV. Journal of Molecular Recognition 2014, 27, 627-639.*
Sela-Culang et al. Frontiers in Immunology 2013; 4:302; p. 1-13.*
Yamazaki, et al., "Expression of Programmed Death 1 Ligands by Murine T Cells and APC1," *The Journal of Immunology*, vol. 169, pp. 5538-5545 (2002).
Butte, et al., "PD-L1 interacts specfically with B7-1 to inhibit T cell proliferation," vol. 27, No. 1, pp. 111-122 (Jul. 2007).
Subudhi et al., "Local expression of B7-H1 promotes organ-specific autoimmunity and transplant rejection," *The Journal of Clinical Investigation*, vol. 113, No. 5, pp. 694-700 (Mar. 2004).
Tamura et al., "B7-H1 costimulation preferentially enhances CD28-independent T-helper cell function," *Blood*, vol. 97, No. 6, pp. 1809-1816 (Mar. 2001).
Nishimura, et al., "Developmentally regulated expression of the PD-1 protein on the surface of double-negative (CD4-CD8-) thymocytes," vol. 8, No. 5, pp. 773-780 (May 1996), [Abstract].
Boettler et al., "Expression of the Interleukin-7 Receptor Alpha Chain (CD127) on Virus-Specific CD8+ T Cells identifies Functionally and Phenotypically Defined Memory T Cells during Acute Resolving Hepatitis B Virus Infection," *J. Virol.* 80, pp. 3532-3540 (Jan. 2006).
Nielsen et al., "Alternative splice variants of the human PD-1 gene," *Cell. Immunol.*, vol. 235, pp. 109-116 (Sep. 2005).
Chen, et al., "Anti-PD-1 / PD-L1 therapy of human cancer: past, present, and future," *The Journal of Clinical Investigation*, vol. 125, pp. 3384-3391 (2015).
Iwai et al., "Involvement of PD-L1 on tumor cells in the escape from host immune system and tumor immunotherapy by PD-L1 blockade," *PNAS*, vol. 99, pp. 12293-12297 (Aug. 2002).
Ohigashi et al., "Clinical Significance of Programmed Death-1Ligand-1 and Programmed Death-1 Ligand-2 Expression in Human Esophageal Cancer," *Clin Cancer Research*, vol. 11, pp. 2947-2953 (2005).
Dong et al., Tumor-associated B7-H1 promotes T-cell apoptosis: a potential mechanism of immune Evasion, *Nat Med*, vol. 8, pp. 793-800 (Jun. 2002).
Kanai et al., "Blockade of B7-H1 Suppresses the Development of Chronic Intestinal Inflammation[1]," *J Immunol.*, vol. 171, pp. 4156-4163 (2003).

(Continued)

*Primary Examiner* — Ilia I Ouspenski
(74) *Attorney, Agent, or Firm* — Gilberto M. Villacorta; Jason N. Mock; Foley & Lardner LLP

(57) ABSTRACT

The present disclosure relates generally to antibodies and functional binding fragments thereof that bind to programmed death-ligand 1 (PD-L1). In particular, the disclosed antibodies and fragments bind to human PD-L1 and comprise novel complementary determining regions (CDRs) also disclosed herein. Finally, the present disclosure relates to administering the disclosed antibodies and fragments to subjects with cancer, thereby treating or slowing the progression or proliferation of the cancer.

31 Claims, 7 Drawing Sheets

Specification includes a Sequence Listing.

(56) References Cited

OTHER PUBLICATIONS

Bird et al., "Single-chain antigen-binding proteins," *Science*, vol. 242, pp. 423-426 (Oct. 1988).
Huston et al., "Protein engineering of antibody binding sites: Recovery of specific activity in an anti-digoxin single-chain Fv analogue produced in *Escherichia coli*," Proc. Natl. Acad. Sci. USA, vol. 85, pp. 5879-5883 (Aug. 1986).
Xu et.al., "Addressing Polyspecificity of Antibodies Selected from an in vitro Yeast Presentation System: a FACS-based, High-Throughput Selection and Analytical Tool," *Protein Engineering, Design and Selection*, vol. 26, No. 10, pp. 10, pp. 663-670 (Sep. 2013).
International Search Report and Written Opinion issued in related International Patent Application No. PCT/US2017/39810, dated Jan. 5, 2018.

\* cited by examiner

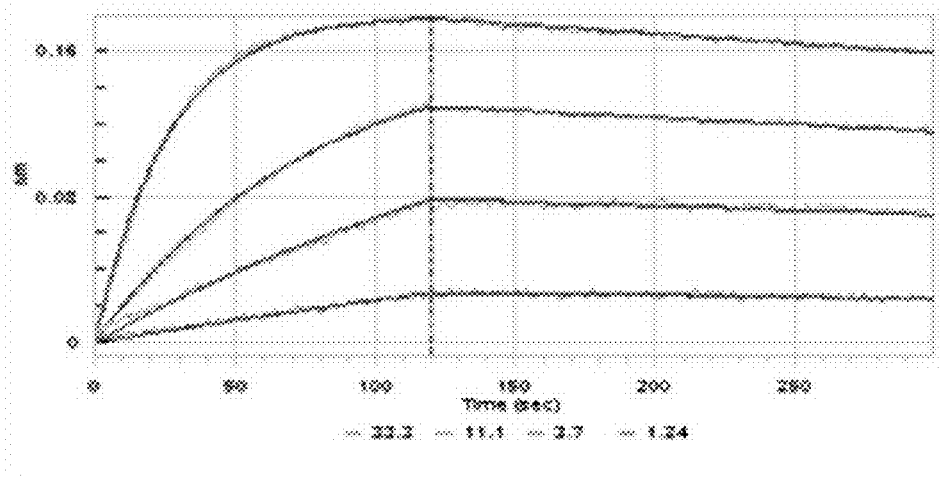
FIGURE 2, CONT'D

PD-L1-SPECIFIC ANTIBODIES AND METHODS OF USING THE SAME

CROSS-REFERENCE TO RELATED APPLICATION

This application claims priority from U.S. Provisional Patent Application No. 62/356,105, filed Jun. 29, 2016. The contents of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 19, 2017, is named 099263-0801_SL.txt and is 43,085 bytes in size.

FIELD OF INVENTION

The present disclosure relates generally to antibodies and functional binding fragments thereof that bind to programmed death-ligand 1 (PD-L1). In particular, the disclosed antibodies and fragments bind to human PD-L1 and comprise novel complementary determining regions (CDRs). Finally, the present disclosure relates to administering the disclosed antibodies and fragments to subjects with cancer, thereby treating or slowing the progression or proliferation of the cancer.

BACKGROUND

PD-L1 (formerly B7-H1) is a B7 family member that is expressed on many cell types, including antigen-presenting cells ("APCs") and activated T cells (Yamazaki et al. (2002) *J. Immunol.* 169:5538). PD-L1 binds to both PD-1 (CD279) and B7-1. Both binding of T-cell-expressed B7-1 by PD-L1 and binding of T-cell-expressed PD-L1 by B7-1 result in T cell inhibition (Butte et al. (2007) *Immunity* 27:111). There is also evidence that, like other B7 family members, PD-L1 can also provide costimulatory signals to T cells (Subudhi et al. (2004) *J. Clin. Invest.* 113:694; Tamura et al. (2001) *Blood* 97:1809). Furthermore, expression of PD-L1 on the cell surface has also been shown to be upregulated through IFN-γ stimulation.

The interaction between PD-1 and its ligand partners PD-L1 (B7-H1; CD274) and PD-L2 (B7-DC; CD273) is an important negative costimulatory signaling pathway involved in the regulation of T cell activation. PD-1 can be expressed on T cells, B cells, natural killer T cells, activated monocytes and dendritic cells (DCs). PD-1 is expressed by activated, but not by unstimulated, human $CD4^+$ and $CD8^+$ T cells, B cells and myeloid cells. Nishimura et al., *Int. Immunol.* 8: 773-80 (1996); Boettler et al., *J. Virol.* 80: 3532-40 (2006). There are at least 4 variants of PD-1 that have been cloned from activated human T cells, including transcripts lacking (i) exon 2, (ii) exon 3. (iii) exons 2 and 3 or (iv) exons 2 through 4. Nielsen et al., *Cell. Immunol.* 235: 109-16 (2005).

Normal human tissues seldom express PD-L1 protein on their cell surface, with the exception of tonsil, placenta, and a small fraction of macrophage-like cells in lung and liver, suggesting that under normal physiological conditions, PD-L1 mRNA is under tight posttranscriptional regulation. In sharp contrast, PD-L1 protein is abundantly expressed on the cell surface in various human cancers, as indicated by Chen & Han, *Anti-PD-1/PD-L1 therapy of human cancer: past, present, and future.* J. CLIN. INVEST. 125, 3384-3391 (2015).

PD-L2 expression, on the other hand, is more restricted than PD-L1. For instance, PD-L2 is inducibly expressed on DCs, macrophages, and bone marrow-derived mast cells.

Additionally, several studies show a receptor for PD-L1 that is independent of PD-1. B7.1 has also been identified as a binding partner for PD-L1. Butte et al., *Immunity* 27: 111-22 (2007). Chemical crosslinking studies suggest that PD-L1 and B7.1 can interact through their IgV-like domains. B7.1:PD-L1 interactions can induce an inhibitory signal into T cells. Ligation of PD-L1 on CD4+ T cells by B7.1 or ligation of B7.1 on CD4+ T cells by PD-L1 delivers an inhibitory signal. T cells lacking CD28 and CTLA-4 show decreased proliferation and cytokine production when stimulated by anti-CD3 plus B7.1 coated beads. In T cells lacking all the receptors for B7.1 (i.e., CD28, CTLA-4 and PD-L1), T cell proliferation and cytokine production were no longer inhibited by anti-CD3 plus B7.1 coated beads. This indicates that B7.1 acts specifically through PD-L1 on the T-cell in the absence of CD28 and CTLA-4. Similarly, T cells lacking PD-1 showed decreased proliferation and cytokine production when stimulated in the presence of anti-CD3 plus PD-L1 coated beads, demonstrating the inhibitory effect of PD-L1 ligation on B7.1 on T cells. When T cells lacking all known receptors for PD-L1 (i.e., no PD-1 and B7.1), T cell proliferation was no longer impaired by anti-CD3 plus PD-L1 coated beads. Thus, PD-L1 can exert an inhibitory effect on T cells either through B7.1 or PD-1.

In the context of human disease, PD-L1 expression has been found in several murine and human cancers, including human lung, ovarian and colon carcinoma and various myelomas (Iwai et al. (2002) *PNAS* 99:12293-7; Ohigashi et al. (2005) *Clin Cancer Res* 11:2947-53). PD-L1 has been suggested to play a role in tumor immunity by increasing apoptosis of antigen-specific T-cell clones (Dong et al. (2002) *Nat Med* 8:793-800). It has also been suggested that PD-L1 might be involved in intestinal mucosal inflammation and inhibition of PD-L1 suppresses wasting disease associated with colitis (Kanai et al. (2003) *J Immunol* 171:4156-63).

As a result, therapeutic targeting of PD-L1 is an area of intense medical interest. The inhibition of PD-L1 signaling has been proposed as a means to enhance T cell immunity for the treatment of cancer (e.g., tumor immunity) and infection, including both acute and chronic (e.g., persistent) infection. However, because only one targeted anti-PD-L1 therapeutic has received marketing approval from the FDA to date, a significant unmet medical need exists.

SUMMARY

The present disclosure provides isolated antibodies, in particular human antibodies that bind to PD-L1 and exhibit desirable therapeutic properties. These properties include high affinity binding to PD-L1, specifically human PD-L1.

In one aspect, the disclosure relates to antibodies or functional fragments thereof that bind to human programmed death-ligand 1 (PD-L1), wherein the antibody or functional fragment thereof comprises: a heavy chain comprising: CDRH1 comprising amino acids 1-3 and 7-9 of SEQ ID NO: 1, wherein amino acids 4-6 are not SSY; CDRH2 comprising amino acids 9-17 of SEQ ID NO: 8; and CDRH3 comprising SEQ ID NO: 15; and a light chain comprising CDRL1 comprising SEQ ID NO: 20; CDRL2 comprising SEQ ID NO: 21; and CDRL3 comprising SEQ ID NO: 22, SEQ ID NO: 75, or SEQ ID NO: 76.

In some embodiments, the CDRH1 region comprises an amino acid sequence selected from the group consisting of SEQ ID NOS: 2, 3, 4, 5, 6, and 7, and in some embodiments the CDRH2 region comprises an amino acid sequence selected from the group consisting of SEQ ID NOS: 8, 9, 10, 11, 12, 13 and 14.

In some embodiments, the variable heavy framework region 1 comprises SEQ ID NO. 26 or SEQ ID NO: 27. In some embodiments, the variable heavy framework region 2 comprises SEQ ID NO. 28, the variable heavy framework region 3 comprises SEQ ID NO. 29, and/or the variable heavy framework region 4 comprises SEQ ID NO. 30.

In some embodiments, the variable light framework region 1 comprises SEQ ID NO. 31, the variable light framework region 2 comprises SEQ ID NO. 32, the variable light framework region 3 comprises SEQ ID NO. 33, SEQ ID NO. 77, or SEQ ID NO. 78, and/or the variable light framework region 4 comprises SEQ ID NO. 34.

In some embodiments, the variable heavy chain sequence comprises an amino acid sequence selected from the group consisting of SEQ ID NOS: 36, 37, 38, 39, 40 and 41. In other embodiments, the variable heavy chain sequence comprises an amino acid sequence selected from the group consisting of SEQ ID NOS: 51, 52, 53, 54, 55, and 56.

In some embodiments, the variable light chain sequence comprises SEQ ID NO: 42.

In some embodiments, the antibody or functional fragment thereof exhibits antibody dependent cellular cytotoxic (ADCC) activity, the antibody or functional fragment thereof exhibits antitumor activity, the antibody or functional fragment thereof inhibits the binding of PD-L1 to PD-1, or the antibody or functional fragment thereof prevents PD-1 mediated inhibition of T-cell activation.

In some embodiments, the antibody or functional fragment thereof is a low fucose antibody or functional fragment thereof, and in some embodiments, the antibody or functional fragment thereof is defucosylated or afucosylated.

In another aspect, the disclosure relates to antibodies or functional fragments thereof that binds to human programmed death-ligand 1 (PD-L1), wherein the antibody or functional fragment thereof comprises a heavy chain comprising SEQ ID NO: 35.

In another aspect, the disclosure relates to antibodies or functional fragments thereof that bind to human programmed death-ligand 1 (PD-L1), wherein the antibody or functional fragment thereof comprises: a heavy chain comprising: CDRH1 comprising SEQ ID NO: 16; CDRH2 comprising SEQ ID NO: 17; and CDRH3 comprising amino acids 6-13 of SEQ ID NO: 18; and a light chain comprising: CDRL1 comprising SEQ ID NO: 23; CDRL2 comprising SEQ ID NO: 24; and CDRL3 comprising SEQ ID NO: 25.

In some embodiments, the CDRH3 comprises SEQ ID NO: 18, and in some embodiments the CDRH3 comprises SEQ ID NO: 19.

In some embodiments, the variable heavy framework region 1 comprises SEQ ID NO. 49, the variable heavy framework region 2 comprises SEQ ID NO. 28, the variable heavy framework region 3 comprises SEQ ID NO. 50, and/or the variable heavy framework region 4 comprises SEQ ID NO. 30.

In some embodiments, the variable light framework region 1 comprises SEQ ID NO. 45, the variable light framework region 2 comprises SEQ ID NO. 46, the variable light framework region 3 comprises SEQ ID NO. 47, and/or the variable light framework region 4 comprises SEQ ID NO. 34.

In some embodiments, the variable heavy chain sequence comprises SEQ ID NO: 48 or 49, and in some embodiments, the variable light chain sequence comprises SEQ ID NO: 50.

In some embodiments, the antibody or functional fragment thereof exhibits antibody dependent cellular cytotoxic (ADCC) activity, the antibody or functional fragment thereof exhibits antitumor activity, the antibody or functional fragment thereof inhibits the binding of PD-L1 to PD-1, or the antibody or functional fragment thereof prevents PD-1 mediated inhibition of T-cell activation.

In some embodiments, the antibody or functional fragment thereof is a low fucose antibody or functional fragment thereof, and in some embodiments, the antibody or functional fragment thereof is defucosylated or afucosylated.

Some embodiments relate to a pharmaceutical composition comprising the disclosed antibodies or functional fragments thereof.

In another aspect, the disclosure relates to methods of inhibiting cancer cell proliferation in a subject, comprising administering the disclosed antibodies or functional fragments thereof to a subject with cancer. For instance, in some embodiments, the disclosure relates to methods of inhibiting tumor cell proliferation in a subject, comprising administering an antibody or functional fragment thereof that binds human PD-L1 with a KD of at least $2.50 \times 10^{-8}$ and CDRH3 comprising amino acids 6-13 of SEQ ID NO: 18 to a subject with cancer. Likewise, in some embodiments, the disclosure relates to methods of inhibiting cancer cell proliferation in a subject, comprising administering an antibody or functional fragment that binds human PD-L1 with a KD of at least $8.30 \times 10^{-9}$ and CDRH3 comprising SEQ ID NO: 15 to a subject with cancer.

In some embodiments, the cancer is a hematological cancer, a neurological cancer, breast cancer, a gastrointestinal cancer, renal cell carcinoma, or a genitourinary cancer. In particular, in some embodiments, the gastrointestinal cancer is colon cancer, the genitourinary cancer is ovarian cancer, prostate cancer or bladder cancer; the hematological cancer is lymphoma. Non-Hodgkin's lymphoma, chronic lymphocytic leukemia, or multiple myeloma; or the renal cell carcinoma is clear cell renal cell carcinoma.

In some embodiments, the cancer is melanoma, lung cancer (such as non-small cell lung cancer), head and neck cancer, liver cancer, pancreatic cancer, bone cancer, or a vascular cancer.

In some embodiments, the cancer is a highly immunogenic carcinoma or the cancer is a PD-L1 expressing cancer.

In some embodiments, the methods further comprise a step of administering to the subject an additional therapeutic compound. For example, in some embodiments, the additional therapeutic compound is a T cell expressing a chimeric antigen receptor (CAR), a tumor-targeting antibody, an immune response potentiating modality, or a small molecule drug.

In some embodiments, the immune response potentiating modality is an anti-GITR antibody, an anti-OX40 antibody, an anti-CD137 antibody, or a TLR agonist.

In some embodiments, the tumor-targeting antibody is an anti-CAIX antibody.

In some embodiments, the small molecule drug is a tumor-targeting small molecule drug, such as a BTK inhibitor, an EGFR inhibitor, a PARP inhibitor, a BET inhibitor, a BRAF inhibitor, or a PI3Kdelta inhibitor.

The foregoing general description and following detailed description are exemplary and explanatory and are intended to provide further explanation of the disclosure as claimed. Other objects, advantages, and novel features will be readily apparent to those skilled in the art from the following brief description of the drawings and detailed description of the disclosure.

DETAILED DESCRIPTION

Figure 1:
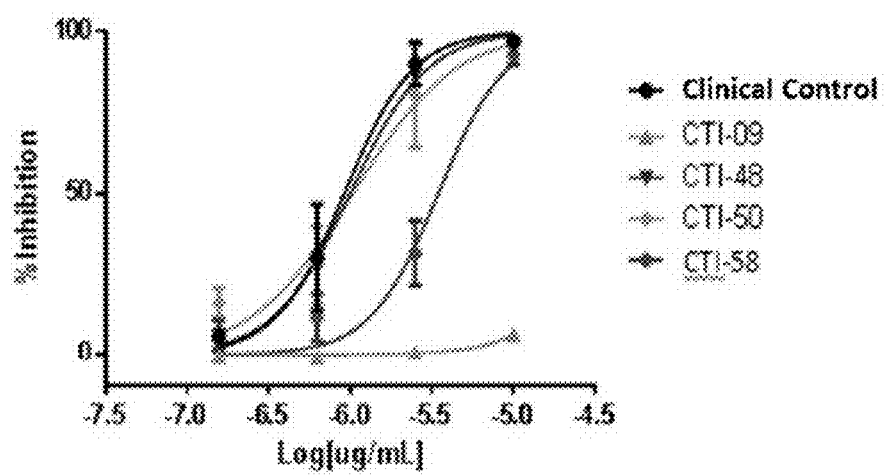
FIG. 1 shows the percent inhibition of PD-1 binding to PD-L-1+ cells by anti-PD-L1 antibodies. The results were obtained using FACS analysis.

The compositions and methods of the present disclosure employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Current Protocols in Molecular Biology* (F. M. Ausubel et al., eds 1987, and periodic updates); *PCR: The Polymerase Chain Reaction*, (Mullis et al., ed., 1994); *A Practical Guide to Molecular Cloning* (Perbal Bernard V., 1988); *Phage Display: A Laboratory Manual* (Barbas et al., 2001).

I. Definitions

It is to be understood that methods are not limited to the particular embodiments described, and as such may vary. It is also to be understood that the terminology used herein is for the purpose of describing particular embodiments only, and is not intended to be limiting. The scope of the present technology will be limited only by the appended claims.

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "about" means plus or minus 10%.

As used herein, "optional" or "optionally" means that the subsequently described event or circumstance may or may not occur, and that the description includes instances where said event or circumstance occurs and instances where it does not.

As used herein, the terms "individual", "patient", or "subject" can be an individual organism, a vertebrate, a mammal (e.g., a bovine, a canine, a feline, or an equine), or a human. In a preferred embodiment, the individual, patient, or subject is a human.

As used herein, the term an "isolated antibody" is intended to refer to an antibody which is substantially free of other antibodies having different antigenic specificities (e.g., an isolated antibody that specifically binds to PD-L1 is substantially free of antibodies that do not bind to PD-L1). An isolated antibody that specifically binds to an epitope of PD-L1 may, however, have cross-reactivity to other proteins, such as PD-L2 or PD-1, as well as proteins from different species. However, the antibody preferably always binds to human PD-L1. In addition, an isolated antibody is typically substantially free of other cellular material and/or chemicals.

As used herein, the term "humanized antibody" refers to an antibody that comprises the CDRs of antibodies derived from mammals other than human, and the framework (FR) region and the constant region of a human antibody. A humanized antibody is useful as an effective component in a therapeutic agent according to the present disclosure since antigenicity of the humanized antibody in human body is lowered.

As used herein, the term "recombinant human antibody" includes all human antibodies that are prepared, expressed, created or isolated by recombinant means, including but not limited to (a) antibodies isolated from an animal (e.g., a mouse) that is transgenic or transchromosomal for human immunoglobulin genes or a hybridoma prepared therefrom, (b) antibodies isolated from a host cell transformed to express the antibody (e.g., from a transfectoma), (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, the term "glycosylation pattern" is defined as the pattern of carbohydrate units that are covalently attached to a protein, more specifically to an immunoglobulin protein.

As used herein, the phrases "therapeutically effective amount" and "therapeutic level" mean that drug dosage or plasma concentration in a subject, respectively, that provides the specific pharmacological effect for which the drug is administered in a subject in need of such treatment, i.e. to reduce, ameliorate, or eliminate the symptoms or effects of cancer, malignant disease, or cancer cell proliferation. It is emphasized that a therapeutically effective amount or therapeutic level of a drug will not always be effective in treating the conditions/diseases described herein, even though such dosage is deemed to be a therapeutically effective amount by those of skill in the art. The therapeutically effective amount may vary based on the route of administration and dosage form, the age and weight of the subject, and/or the subject's condition, including the type and stage of the cancer, malignant disease, or cancer cell proliferation, among other factors.

The term "highly immunogenic cancer" refers to cancers that have been infiltrated with T cells or lymphocytes or have developed a similar lymphatic response. In many instances, tumor immunogenicity is believed to be associated with increased rate of mutations. In this way, the more mutations a tumor has, the higher the chance that the tumor antigens can trigger an immune response.

The terms "treatment" or "treating" as used herein with reference to cancer, malignant disease, or cancer cell proliferation refer to reducing, ameliorating or eliminating one or more symptoms or effects of cancer, malignant disease, or cancer cell proliferation.

II. Anti-PD-L1 Antibodies

Provided herein are anti-PD-L1 antibodies that may be used, among other reasons, to treat cancer. The anti-PD-L1 antibodies of the present disclosure are believed to enhance co-stimulation of the host immune response through antagonism of at least one negative costimulatory signal attributable to PD-L1.

The disclosed anti-PD-L1 antibodies and functional fragments thereof will have a variety of functional properties for treating cancers or malignant disease, including but not limited to having antibody dependent cellular cytotoxic (ADCC) activity, having antitumor activity, inhibiting the binding of PD-L1 to PD-1, and preventing PD-1 mediated inhibition of T-cell activation.

Further, as a result of the antagonism of signaling through PD-L1, including blocking PD-L1 from interacting with either PD-1, B7.1 or both, the disclosed antibodies and functional fragments will prevent PD-L1 from sending a negative costimulatory signal to T-cells and other antigen presenting cells, thus enhancing anti-tumor immunity and the immunological defense against cancer and malignant disease. In addition, the disclosed anti-PD-L1 antibodies and functional fragments, may be combined with additional therapeutic compounds, including but not limited to, CAR T cells (e.g., modified T cells that express an anti-CD19, anti-CAIX, anti-IL13Ra2, or anti-PD-L1 CAR), other tumor-targeting antibodies (e.g., an anti-CAIX antibody), immune response potentiating modalities (e.g., an anti-GITR antibody, an anti-OX40 antibody, an anti-CD137 antibody, or a TLR agonist), and small molecule drugs (e.g., a BTK inhibitor, an EGFR inhibitor, a BET inhibitor, a PI3Kdelta inhibitor, a BRAF inhibitor, or a PARP inhibitor).

The disclosed antibodies can be polyclonal, monoclonal, chimeric, human, partially or fully humanized, and/or recombinant. For example, in some embodiments, the anti-PD-L1 antibody is a polyclonal antibody or a PD-L1-binding functional fragment thereof. In some embodiments, the anti-PD-L1 antibody is a monoclonal antibody or a PD-L1-binding functional fragment thereof. In some embodiments, the antibodies and functional fragments thereof can bind human, cyno, and/or murine PD-L1.

Polyclonal antibodies may be obtained by methods known in the art, such as by immunizing a selected animal with a PD-L1 antigen, collecting serum from the animal, and isolating and/or purifying antibodies from the serum. Monoclonal antibodies (mAbs) may be obtained by methods known in the art, for example, by fusing antibody-producing cells with immortalized cells to obtain a hybridoma, and/or by generating mAbs from mRNA extracted from bone marrow and spleen cells of immunized animals using combinatorial antibody library technology. Recombinant antibodies may be obtained by methods known in the art, for example, using phage or yeast display technologies and/or expressing or co-expressing antibody polypeptides. Other techniques for making antibodies are known in the art, and can be used to obtain antibodies used in the methods described herein.

Typically, an antibody consists of four polypeptides: two identical copies of a heavy (H) chain polypeptide and two copies of a light (L) chain polypeptide. Typically, each heavy chain contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody.

The terms "PD-L1-binding functional fragment" or "functional fragment," as used herein, refer to one or more fragments of an anti-PD-L1 antibody that retain the ability to bind PD-L1. Examples of binding fragments include (i) Fab fragments (monovalent fragments consisting of the VL, VH, CL and CH1 domains); (ii) F(ab')2 fragments (bivalent fragment comprising two Fab fragments linked by a disulfide bridge at the hinge region); (iii) Fd fragments (comprising the VH and CH1 domains); (iv) Fv fragments (comprising the VL and VH domains of a single arm of an antibody), (v) dAb fragments (comprising a VH domain); and (vi) isolated complementarity determining regions (CDR), e.g., VH CDR3. Other examples include single chain Fv (scFv) constructs. See e.g., Bird et al., Science, 242:423-26 (1988); Huston et al., Proc. Natl. Acad. Sci. USA, 85:5879-83 (1988). Other examples include PD-L1-binding-domain immunoglobulin fusion proteins comprising (i) a PD-L1-binding domain polypeptide (such as a heavy chain variable region, a light chain variable region, or a heavy chain variable region fused to a light chain variable region via a linker peptide) fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region.

The hinge region of the disclosed antibodies may be modified by replacing one or more cysteine residues with, for example, serine residues, to prevent dimerization. See, e.g., U.S. Patent Application Publication 2003/0118592; U.S. Patent Application Publication U.S. 2003/0133939. Additionally, in some embodiments, the disclosed antibodies may comprise other mutations, including but not limited to a variant Fc portion of an IgG having the point mutations S239D/I332E, S239D, or I332E, or any combination thereof, or a variant Fc portion of an IgG4 having the point mutation S228P. Such modifications may alter the binding of the disclosed antibodies and functional fragments to Fc receptors (FcRs), and in some embodiments, the antibody may be modified to be more stable, while in some embodiments, the antibody may be modified to enhance ADCC function. When determining the number of the residue, the Kabat numbering of residues may be determined for a given antibody by alignment at regions of homology of the sequence of the antibody with a "standard" Kabat numbered sequence.

In some embodiments, the glycosylation patterns of the disclosed antibodies may be modified or altered. For instance, in some embodiments, the disclosed antibodies and functional fragments thereof may be low fucose antibodies or they may be defucosylated or the antibodies may be expressed or produced in such a way that they are lacking fucose altogether (i.e. afucosylated). Modifying the fucose content of the antibody or functional fragment may be accomplished through various means known in the art, for instance, expressing the antibody or functional fragment in a cell that is FUT8 deficient or that has a mutated version of FUT8. Low fucose or defucosylated antibodies and functional fragment have increased ADCC activity. In addition to alterations in fucose, the disclosed antibodies and functional fragments may comprise other functional modifications to their glycosylation patterns. For instance, modifications at position 297 (e.g. N297A and N297Q) can prevent glycosylation of the Fc region altogether, thus eliminating Fc function, ADCC, and CDC.

In some embodiments, the anti-PD-L1 antibody is CTI-07, CTI-09, CTI-48, CTI-49, CTI-50, CTI-76, CTI-77, CTI-78, CTI-57, or CTI-58 or a functional fragment thereof. Tables 1 and 2 provides exemplary CDR sequences of the disclosed anti-PD-L1 antibodies and functional fragments thereof.

TABLE 1

| Anitbody | HCDR1 | HCDR2 | HCDR3 |
|---|---|---|---|
| CTI-48 | GTFSRSAIS (SEQ ID NO: 2) | VIIPAFGEANYAQKFQG (SEQ ID NO: 9) | ARGRQMFGAGIDF (SEQ ID NO: 15) |
| CTI-49 | GTFSGYAIS (SEQ ID NO: 3) | VIIPAFGTANYAQKFQG (SEQ ID NO: 10) | ARGRQMFGAGIDF (SEQ ID NO: 15) |
| CTI-76 | GTFWRYAIS (SEQ ID NO: 4) | VIIPIWGKANYAQKFQG (SEQ ID NO: 11) | ARGRQMFGAGIDF (SEQ ID NO: 15) |
| CTI-77 | GTGGSYAIS (SEQ ID NO: 5) | GIYPAFGTANYAQKFQG (SEQ ID NO: 12) | ARGRQMFGAGIDF (SEQ ID NO: 15) |
| CTI-78 | GTFGTYAIS (SEQ ID NO: 6) | GIYPRFGTANYAQKFQG (SEQ ID NO: 13) | ARGRQMFGAGIDF (SEQ ID NO: 15) |
| CTI-50 | GTFSPKAIS (SEQ ID NO: 7) | VIIPIFGPANYAKFQG (SEQ ID NO: 14) | ARGRQMFGAGIDF (SEQ ID NO: 15) |
| CTI-57 | YTLSSHGIT (SEQ ID NO: 16) | WISAHSGHASNAQKVED (SEQ ID NO: 17) | ARVWRALYHGMDV (SEQ ID NO: 18) |
| CTI-58 | YTLSSHGIT (SEQ ID NO: 16) | WISAHSGHASNAQKVED (SEQ ID NO: 17) | ARVHAALYHGMDV (SEQ ID NO: 19) |
| CTI-09 | GTFSSYAIS (SEQ ID NO: 1) | GIIPIFGTANYAQKFQG (SEQ ID NO: 8) | ARGRQMFGAGIDF (SEQ ID NO: 15) |
| CTI-07 | YTLSSHGIT (SEQ ID NO: 16) | WISAHSGHASNAQKVED (SEQ ID NO: 17) | ARVHAALYYGMDV (SEQ ID NO: 57) |
| CTI-97 | GTFSRSAIS (SEQ ID NO: 2) | VIIPAFGEANYAQKFQG (SEQ ID NO: 9) | ARGRQMFGAGIDF (SEQ ID NO: 15) |
| CTI-98 | GTFSRSAIS (SEQ ID NO: 2) | VIIPAFGEANYAQKFQG (SEQ ID NO: 9) | ARGRQMFGAGIDF (SEQ ID NO: 15) |
| CTI-92 | GTFSRSAIS (SEQ ID NO: 2) | VIIPAFGEANYAQKFQG (SEQ ID NO: 9) | ARGRQMFGAGIDF (SEQ ID NO: 15) |
| CTI-95 | GTFSRSAIS (SEQ ID NO: 2) | VIIPAFGEANYAQKFQG (SEQ ID NO: 9) | ARGRQMFGAGIDF (SEQ ID NO: 15) |
| CTI-93 | GTFSRSAIS (SEQ ID NO: 2) | VIIPAFGEANYAQKFQG (SEQ ID NO: 9) | ARGRQMFGAGIDF (SEQ ID NO: 15) |
| CTI-94 | GTFSRSAIS (SEQ ID NO: 2) | VIIPAFGEANYAQKFQG (SEQ ID NO: 9) | ARGRQMFGAGIDF (SEQ ID NO: 15) |
| CTI-96 | GTFSRSAIS (SEQ ID NO: 2) | VIIPAFGEANYAQKFQG (SEQ ID NO: 9) | ARGRQMFGAGIDF (SEQ ID NO: 15) |

TABLE 2

| Anitbody | LCDR1 | LCDR2 | LCDR3 |
|---|---|---|---|
| CTI-48 | TRSSGSIDSNYVQ (SEQ ID NO: 20) | EDNQRPS (SEQ ID NO: 21) | QSYDSNNRHVI (SEQ ID NO: 22) |
| CTI-49 | TRSSGSIDSNYVQ (SEQ ID NO: 20) | EDNQRPS (SEQ ID NO: 21) | QSYDSNNRHVI (SEQ ID NO: 22) |
| CTI-76 | TRSSGSIDSNYVQ (SEQ ID NO: 20) | EDNQRPS (SEQ ID NO: 21) | QSYDSNNRHVI (SEQ ID NO: 22) |
| CTI-77 | TRSSGSIDSNYVQ (SEQ ID NO: 20) | EDNQRPS (SEQ ID NO: 21) | QSYDSNNRHVI (SEQ ID NO: 22) |
| CTI-78 | TRSSGSIDSNYVQ (SEQ ID NO: 20) | EDNQRPS (SEQ ID NO: 21) | QSYDSNNRHVI (SEQ ID NO: 22) |
| CTI-50 | TRSSGSIDSNYVQ (SEQ ID NO: 20) | EDNQRPS (SEQ ID NO: 21) | QSYDSNNRHVI (SEQ ID NO: 22) |
| CTI-57 | GGNNIGSKGVH (SEQ ID NO: 23) | DDSDRPS (SEQ ID NO: 24) | QVWDSSSDHWV (SEQ ID NO: 25) |
| CTI-58 | GGNNIGSKGVH (SEQ ID NO: 23) | DDSDRPS (SEQ ID NO: 24) | QVWDSSSDHWV (SEQ ID NO: 25) |
| CTI-09 | TRSSGSIDSNYVQ (SEQ ID NO: 20) | EDNQRPS (SEQ ID NO: 21) | QSYDSNNRHVI (SEQ ID NO: 22) |
| CTI-07 | GGNNIGSKGVH (SEQ ID NO: 23) | DDSDRPS (SEQ ID NO: 24) | QVWDSSSDHWV (SEQ ID NO: 25) |
| CTI-97 | TRSSGSIDSNYVQ (SEQ ID NO: 20) | EDNQRPS (SEQ ID NO: 21) | QSYDSNLRHVI (SEQ ID NO: 75) |
| CTI-98 | TRSSGSIDSNYVQ (SEQ ID NO: 20) | EDNQRPS (SEQ ID NO: 21) | QSYDSNLRHVI (SEQ ID NO: 75) |
| CTI-92 | TRSSGSIDSNYVQ (SEQ ID NO: 20) | EDNQRPS (SEQ ID NO: 21) | QSYDSNNRHVI (SEQ ID NO: 22) |
| CTI-95 | TRSSGSIDSNYVQ (SEQ ID NO: 20) | EDNQRPS (SEQ ID NO: 21) | QSYDSNNRHVI (SEQ ID NO: 22) |
| CTI-93 | TRSSGSIDSNYVQ (SEQ ID NO: 20) | EDNQRPS (SEQ ID NO: 21) | QSYDSNIRHVI (SEQ ID NO: 76) |
| CTI-94 | TRSSGSIDSNYVQ (SEQ ID NO: 20) | EDNQRPS (SEQ ID NO: 21) | QSYDSNLRHVI (SEQ ID NO: 75) |
| CTI-96 | TRSSGSIDSNYVQ (SEQ ID NO: 20) | EDNQRPS (SEQ ID NO: 21) | QSYDSNIRHVI (SEQ ID NO: 76) |

Additionally, the disclosed antibodies and functional fragments may also comprise various framework regions. For instance, in some embodiments the disclosed antibodies and functional fragments comprise SEQ ID NOs 26-34 and/or 43-47. In some embodiments, certain alterations to the framework regions may be particularly advantageous. For instance, substituting glutamic acid (E) for glutamine (Q) in the first position of framework region one of the heavy chain of an antibody can increase manufacturing product stability efficiency. Accordingly, some embodiments of the disclosed antibodies and fragments will incorporate this modification. Thus, in some embodiments, the heavy chain of the disclosed antibodies or functional fragments will comprise SEQ ID NOs: 36-41, while in other embodiments, the heavy chain of the disclosed antibodies or functional fragments will comprise SEQ ID NOs: 48-49 or 51-56. Furthermore, in some embodiments, the heavy chain of the disclosed antibodies or functional fragments will comprise SEQ ID NOs: 71-72, or polypeptide encoded by a nucleic acid sequence comprising SEQ ID NOs: 59-68.

In some embodiments, the light chain of the disclosed antibodies or functional fragments will comprise SEQ ID NOs: 42 or 50. Furthermore, in some embodiments, the light chain of the disclosed antibodies or functional fragments will comprise a polypeptide encoded by a nucleic acid sequence comprising SEQ ID NOs: 69-70.

One of ordinary skill in the art will understand that certain changes can be made to the disclosed sequences without compromising the binding affinity or function of the disclosed anti-PD-L1 antibodies and functional fragments. According, in some embodiments, the anti-PD-L1 antibodies or functional fragments will share about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the disclosed sequences.

In some embodiments, the disclosure provides for isolated nucleic acid sequences encoding an anti-PD-L1 antibody or functional fragment thereof, for examples, SEQ ID NOs: 59-70.

The disclosed antibodies and functional fragments thereof may be defined by sequence, or by functional characteristics.

For instance, the disclosed antibodies and functional fragments thereof, can have a $K_D$ of at least $3.0\times10^{-8}$, at least $2.5\times10^{-8}$, at least $2.0\times10^{-8}$, at least $1.5\times10^{-8}$, at least $1.0\times10^{-8}$, at least $0.5\times10^{-8}$, at least $9.95\times10^{-9}$, at least $9.90\times10^{-9}$, at least $9.85\times10^{-9}$, at least $9.80\times10^{-9}$, at least $9.75\times10^{-9}$, at least $9.70\times10^{-9}$, at least $9.65\times10^{-9}$, at least $9.60\times10^{-9}$, at least $9.55\times10^{-9}$, at least $9.5\times10^{-9}$, at least $9.45\times10^{-9}$, at least $9.40\times10^{-9}$, at least $9.35\times10^{-9}$, at least $9.30\times10^{-9}$, at least $9.25\times10^{-9}$, at least $9.20\times10^{-9}$, at least $9.15\times10^{-9}$, at least $9.10\times10^{-9}$, at least $9.05\times10^{-9}$, at least $9.0\times10^{-9}$, at least $8.95\times10^{-9}$, at least $8.90\times10^{-9}$, at least $8.85\times10^{-9}$, at least $8.80\times10^{-9}$, at least $8.75\times10^{-9}$, at least $8.70\times10^{-9}$, at least $8.65\times10^{-9}$, at least $8.60\times10^{-9}$, at least $8.55\times10^{-9}$, at least $8.5\times10^{-9}$, at least $8.45\times10^{-9}$, at least $8.40\times10^{-9}$, at least $8.35\times10^{-9}$, at least $8.30\times10^{-9}$, at least $8.25\times10^{-9}$, at least $8.20\times10^{-9}$, at least $8.15\times10^{-9}$, at least $8.10\times10^{-9}$, at least $8.05\times10^{-9}$, at least $8.0\times10^{-9}$, at least $7.95\times10^{-9}$, at least $7.90\times10^{-9}$, at least $7.85\times10^{-9}$, at least $7.80\times10^{-9}$, at least $7.75\times10^{-9}$, at least $7.70\times10^{-9}$, at least $7.65\times10^{-9}$, at least $7.60\times10^{-9}$, at least $7.55\times10^{-9}$, at least $7.5\times10^{-9}$, at least $7.45\times10^{-9}$, at least $7.40\times10^{-9}$, at least $7.35\times10^{-9}$, at least $7.30\times10^{-9}$, at least $7.25\times10^{-9}$, at least $7.20\times10^{-9}$, at least $7.15\times10^{-9}$, at least $7.10\times10^{-9}$, at least $7.05\times10^{-9}$, at least $7.0\times10^{-9}$, at least $6.95\times10^{-9}$, at least $6.90\times10^{-9}$, at least $6.85\times10^{-9}$, at least $6.80\times10^{-9}$, at least $6.75\times10^{-9}$, at least $6.70\times10^{-9}$, at least $6.65\times10^{-9}$, at least $6.60\times10^{-9}$, at least $6.55\times10^{-9}$, at least $6.5\times10^{-9}$, at least $6.45\times10^{-9}$, at least $6.40\times10^{-9}$, at least $6.35\times10^{-9}$, at least $6.30\times10^{-9}$, at least $6.25\times10^{-9}$, at least $6.20\times10^{-9}$, at least $6.15\times10^{-9}$, at least $6.10\times10^{-9}$, at least $6.05\times10^{-9}$, at least $6.0\times10^{-9}$, at least $5.95\times10^{-9}$, at least $5.90\times10^{-9}$, at least $5.85\times10^{-9}$, at least $5.80\times10^{-9}$, at least $5.75\times10^{-9}$, at least $5.70\times10^{-9}$, at least $5.65\times10^{-9}$, at least $5.60\times10^{-9}$, at least $5.55\times10^{-9}$, at least $5.5\times10^{-9}$, at least $5.45\times10^{-9}$, at least $5.40\times10^{-9}$, at least $5.35\times10^{-9}$, at least $5.30\times10^{-9}$, at least $5.25\times10^{-9}$, at least $5.20\times10^{-9}$, at least $5.15\times10^{-9}$, at least $5.10\times10^{-9}$, at least $5.05\times10^{-9}$, at least $5.0\times10^{-9}$, at least $4.95\times10^{-9}$, at least $4.90\times10^{-9}$, at least $4.85\times10^{-9}$, at least $4.80\times10^{-9}$, at least $4.75\times10^{-9}$, at least $4.70\times10^{-9}$, at least $4.65\times10^{-9}$, at least $4.60\times10^{-9}$, at least $4.55\times10^{-9}$, at least $4.5\times10^{-9}$, at least $4.45\times10^{-9}$, at least $4.40\times10^{-9}$, at least $4.35\times10^{-9}$, at least $4.30\times10^{-9}$, at least $4.25\times10^{-9}$, at least $4.20\times10^{-9}$, at least $4.15\times10^{-9}$, at least $4.10\times10^{-9}$, at least $4.05\times10^{-9}$, at least $4.0\times10^{-9}$, at least $3.95\times10^{-9}$, at least $3.90\times10^{-9}$, at least $3.85\times10^{-9}$, at least $3.80\times10^{-9}$, at least $3.75\times10^{-9}$, at least $3.70\times10^{-9}$, at least $3.65\times10^{-9}$, at least $3.60\times10^{-9}$, at least $3.55\times10^{-9}$, at least $3.5\times10^{-9}$, at least $3.45\times10^{-9}$, at least $3.40\times10^{-9}$, at least $3.35\times10^{-9}$, at least $3.30\times10^{-9}$, at least $3.25\times10^{-9}$, at least $3.20\times10^{-9}$, at least $3.15\times10^{-9}$, at least $3.10\times10^{-9}$, at least $3.05\times10^{-9}$, at least $3.0\times10^{-9}$, at least $2.95\times10^{-9}$, at least $2.90\times10^{-9}$, at least $2.85\times10^{-9}$, at least $2.80\times10^{-9}$, at least $2.75\times10^{-9}$, at least $2.70\times10^{-9}$, at least $2.65\times10^{-9}$, at least $2.60\times10^{-9}$, at least $2.55\times10^{-9}$, at least $2.5\times10^{-9}$, at least $2.45\times10^{-9}$, at least $2.40\times10^{-9}$, at least $2.35\times10^{-9}$, at least $2.30\times10^{-9}$, at least $2.25\times10^{-9}$, at least $2.20\times10^{-9}$, at least $2.15\times10^{-9}$, at least $2.10\times10^{-9}$, at least $2.05\times10^{-9}$, at least $2.0\times10^{-9}$, at least $1.95\times10^{-9}$, at least $1.90\times10^{-9}$, at least $1.85\times10^{-9}$, at least $1.80\times10^{-9}$, at least $1.75\times10^{-9}$, at least $1.70\times10^{-9}$, at least $1.65\times10^{-9}$, at least $1.60\times10^{-9}$, at least $1.55\times10^{-9}$, at least $1.5\times10^{-9}$, at least $1.45\times10^{-9}$, at least $1.40\times10^{-9}$, at least $1.35\times10^{-9}$, at least $1.30\times10^{-9}$, at least $1.25\times10^{-9}$, at least $1.20\times10^{-9}$, at least $1.15\times10^{-9}$, at least $1.10\times10^{-9}$, at least $1.05\times10^{-9}$, at least $1.0\times10^{-9}$, at least $0.95\times10^{-9}$, at least $0.90\times10^{-9}$, at least $0.85\times10^{-9}$, at least $0.80\times10^{-9}$, at least $0.75\times10^{-9}$, at least $0.70\times10^{-9}$, at least $0.65\times10^{-9}$, at least $0.60\times10^{-9}$, at least $0.55\times10^{-9}$, at least $0.5\times10^{-9}$, at least $0.45\times10^{-9}$, at least $0.40\times10^{-9}$, at least $0.35\times10^{-9}$, at least $0.30\times10^{-9}$, at least $0.25\times10^{-9}$, at least $0.20\times10^{-9}$, at least $0.15\times10^{-9}$, at least $0.10\times10^{-9}$, at least $0.05\times10^{-9}$, at least $9.5\times10^{-10}$, at least $9.0\times10^{-10}$, at least $8.5\times10^{-10}$, at least $8.0\times10^{-10}$, or any value in between. For example, the disclosed antibodies and functional fragments thereof can have $K_D$ values of $8.2\times10^{-10}$, $2.31\times10^{-09}$, $8.24\times10^{-09}$, $3.25\times10^{-09}$, $3.46\times10^{-09}$, $1.91\times10^{-09}$, $7.97\times10^{-08}$, $2.41\times10^{-08}$, $9.5\times10^{-10}$, or $8.6\times10^{-10}$.

Likewise, the disclosed antibodies and functional fragments thereof can have $IC_{50}$ values between $4.0\times10^{-5}$ µg/ml and $9.5\times10^{-7}$ µg/ml or any value in between. For example, the disclosed antibodies and functional fragments thereof can have $IC_{50}$ values of $9.19\times10^{-7}$, $4.156\times10^{-5}$, $9.985\times10^{-7}$, $1.037\times10^{-6}$ or $3.463\times10^{-6}$.

The anti-PD-L1 antibody or a PD-L1-binding functional fragment thereof can be formulated in a pharmaceutical composition suitable for administration to the target subject by the intended route of administration, as discussed in more detail below.

III. Pharmaceutical Compositions and Formulations

Pharmaceutical compositions suitable for use in the methods described herein can include the therapeutically active agent (e.g., anti-PD-L1 antibodies or functional fragments thereof) and a pharmaceutically acceptable carrier or diluent.

The composition may be formulated for intravenous, subcutaneous, intraperitoneal, intramuscular, oral, nasal, pulmonary, ocular, vaginal, or rectal administration. In some embodiments, anti-PD-L1 antibodies or functional fragments thereof are formulated for intravenous, subcutaneous, intraperitoneal, or intramuscular administration, such as in a solution, suspension, emulsion, liposome formulation, etc. The pharmaceutical composition can be formulated to be an immediate-release composition, sustained-release composition, delayed-release composition, etc., using techniques known in the art.

Pharmacologically acceptable carriers for various dosage forms are known in the art. For example, excipients, lubricants, binders, and disintegrants for solid preparations are known; solvents, solubilizing agents, suspending agents, isotonicity agents, buffers, and soothing agents for liquid preparations are known. In some embodiments, the pharmaceutical compositions include one or more additional components, such as one or more preservatives, antioxidants, stabilizing agents and the like.

Additionally, the disclosed pharmaceutical compositions can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In some embodiment, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Pharmaceutical compositions of the disclosure can be administered in combination with other therapeutics. For example, the combination therapy can include a pharmaceutical composition comprising at least one of the disclosed anti-PD-L1 antibodies or functional fragments thereof with at least one or more additional therapeutic agents, including but not limited to, CAR T cells (e.g., modified T cells that express an anti-CD19, anti-Her2, anti-BCMA, anti-CS-1, anti-PSCA, anti-CAIX, anti-IL13R, or anti-PD-L1 CAR), other tumor-targeting antibodies (e.g., an anti-CAIX antibody), immune response potentiating modalities (e.g., an anti-GITR antibody, an anti-OX40 antibody, an anti-CD137 antibody, or a TLR agonist), and small molecule drugs (e.g., a BTK inhibitor, an EGFR inhibitor, a BET inhibitor, a PI3Kdelta inhibitor, a BRAF inhibitor, or a PARP inhibitor). The pharmaceutical compositions of the disclosure can also be administered in conjunction with radiation therapy.

IV. Methods of Treating Cancer

Provided herein are methods of treating cancer, malignant disease, or cancer cell proliferation with the disclosed anti-PD-L1 antibodies. More specifically, the disclosure provides for methods of enhancing T-cell function and anti-tumor immunity comprising administering a therapeutically effective amount of any of the above described anti-PD-L1 antibodies or compositions.

Enhancing T-cell function and anti-tumor immunity provides a broad spectrum approach to treating cancer, malignant disease, or cancer cell proliferation. Accordingly, numerous types of cancer can be treated by administering the disclosed anti-PD-L1 antibodies and functional fragments thereof. For example, in some embodiments, the cancer is a hematological cancer (e.g., lymphoma, Non-Hodgkin's lymphoma, chronic lymphocytic leukemia, or multiple myeloma), a neurological cancer, breast cancer, a gastrointestinal cancer (e.g., colon cancer), renal cell carcinoma (e.g., clear cell renal cell carcinoma), or a genitourinary cancer (e.g., ovarian cancer). In some embodiments, the cancer is melanoma, lung cancer (e.g., non-small cell lung cancer), head and neck cancer, liver cancer, pancreatic cancer, bone cancer, prostate cancer, bladder cancer, or a vascular cancer.

In some embodiments, the cancer being treated according to the disclosed methods is a highly immunogenic carcinoma. And in some embodiments, the cancer being treated according to the disclosed methods is a cancer that expresses PD-L1.

Dosage regimens are adjusted to provide the optimum desired response (e.g., a therapeutic response like tumor regression or remission). For example, in some embodiments, a single bolus may be administered, while in some embodiments, several divided doses may be administered over time or the dose may be proportionally reduced or increased as indicated by the situation. For example, in some embodiments the disclosed antibodies or functional fragments may be administered once or twice weekly by subcutaneous or intravenous injection. In some embodiments, the disclosed antibodies or functional fragments may be administered once or twice monthly by subcutaneous injection. In some embodiments, the disclosed antibodies or functional fragments may be administered once every week, once every other week, once every three weeks, once every four weeks, once every other month, once every three months, once every four months, once every five months, or once every six months.

Exemplary doses can vary according to the size and health of the individual being treated, as well as the condition being treated. For example, in some embodiments, the disclosed antibodies or functional fragments may be administered in a dose of 1-100 mg/kg. In some embodiments, the disclosed antibodies and functional fragments may be administered in a dose of 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 mg/kg.

Furthermore, the disclosed methods of treatment can additionally comprise the administration of a second therapeutic compound in addition to the anti-PD-L1 antibody or functional fragment thereof. For example, in some embodiments, the additional therapeutic compound is a CAR-T cell, a tumor-targeting antibody, an immune response potentiating modality, or a small molecule drug.

In some embodiments, the disclosed methods may utilize antibodies and functional fragments thereof with various functional characteristics. For instance, the disclosed methods can comprise anti-PD-L1 antibodies and functional fragments thereof, having a $K_D$ of at least $3.0 \times 10^{-8}$, at least $2.5 \times 10^{-8}$, at least $2.0 \times 10^{-8}$, at least $1.5 \times 10^{-8}$, at least $1.0 \times 10^{-8}$, at least $0.5 \times 10^{-8}$, at least $9.95 \times 10^{-9}$, at least $9.90 \times 10^{-9}$, at least $9.85 \times 10^{-9}$, at least $9.80 \times 10^{-9}$, at least $9.75 \times 10^{-9}$, at least $9.70 \times 10^{-9}$, at least $9.65 \times 10^{-9}$, at least $9.60 \times 10^{-9}$, at least $9.55 \times 10^{-9}$, at least $9.5 \times 10^{-9}$, at least $9.45 \times 10^{-9}$, at least $9.40 \times 10^{-9}$, at least $9.35 \times 10^{-9}$, at least $9.30 \times 10^{-9}$, at least $9.25 \times 10^{-9}$, at least $9.20 \times 10^{-9}$, at least $9.15 \times 10^{-9}$, at least $9.10 \times 10^{-9}$, at least $9.05 \times 10^{-9}$, at least $9.0 \times 10^{-9}$, at least $8.95 \times 10^{-9}$, at least $8.90 \times 10^{-9}$, at least $8.85 \times 10^{-9}$, at least $8.80 \times 10^{-9}$, at least $8.75 \times 10^{-9}$, at least $8.70 \times 10^{-9}$, at least $8.65 \times 10^{-9}$, at least $8.60 \times 10^{-9}$, at least $8.55 \times 10^{-9}$, at least $8.5 \times 10^{-9}$, at least $8.45 \times 10^{-9}$, at least $8.40 \times 10^{-9}$, at least $8.35 \times 10^{-9}$, at least $8.30 \times 10^{-9}$, at least $8.25 \times 10^{-9}$, at least $8.20 \times 10^{-9}$, at least $8.15 \times 10^{-9}$, at least $8.10 \times 10^{-9}$, at least $8.05 \times 10^{-9}$, at least $8.0 \times 10^{-9}$, at least $7.95 \times 10^{-9}$, at least $7.90 \times 10^{-9}$, at least $7.85 \times 10^{-9}$, at least $7.80 \times 10^{-9}$, at least $7.75 \times 10^{-9}$, at least $7.70 \times 10^{-9}$, at least $7.65 \times 10^{-9}$, at least $7.60 \times 10^{-9}$, at least $7.55 \times 10^{-9}$, at least $7.5 \times 10^{-9}$, at least $7.45 \times 10^{-9}$, at least $7.40 \times 10^{-9}$, at least $7.35 \times 10^{-9}$, at least $7.30 \times 10^{-9}$, at least $7.25 \times 10^{-9}$, at least $7.20 \times 10^{-9}$, at least $7.15 \times 10^{-9}$, at least $7.10 \times 10^{-9}$, at least $7.05 \times 10^{-9}$, at least $7.0 \times 10^{-9}$, at least $6.95 \times 10^{-9}$, at least $6.90 \times 10^{-9}$, at least $6.85 \times 10^{-9}$, at least $6.80 \times 10^{-9}$, at least $6.75 \times 10^{-9}$, at least $6.70 \times 10^{-9}$, at least $6.65 \times 10^{-9}$, at least $6.60 \times 10^{-9}$, at least $6.55 \times 10^{-9}$, at least $6.5 \times 10^{-9}$, at least $6.45 \times 10^{-9}$, at least $6.40 \times 10^{-9}$, at least $6.35 \times 10^{-9}$, at least $6.30 \times 10^{-9}$, at least $6.25 \times 10^{-9}$, at least $6.20 \times 10^{-9}$, at least $6.15 \times 10^{-9}$, at least $6.10 \times 10^{-9}$, at least $6.05 \times 10^{-9}$, at least $6.0 \times 10^{-9}$, at least $5.95 \times 10^{-9}$, at least $5.90 \times 10^{-9}$, at least $5.85 \times 10^{-9}$, at least $5.80 \times 10^{-9}$, at least $5.75 \times 10^{-9}$, at least $5.70 \times 10^{-9}$, at least $5.65 \times 10^{-9}$, at least $5.60 \times 10^{-9}$, at least $5.55 \times 10^{-9}$, at least $5.5 \times 10^{-9}$, at least $5.45 \times 10^{-9}$, at least $5.40 \times 10^{-9}$, at least $5.35 \times 10^{-9}$, at least $5.30 \times 10^{-9}$, at least $5.25 \times 10^{-9}$, at least $5.20 \times 10^{-9}$, at least $5.15 \times 10^{-9}$, at least $5.10 \times 10^{-9}$, at least $5.05 \times 10^{-9}$, at least $5.0 \times 10^{-9}$, at least $4.95 \times 10^{-9}$, at least $4.90 \times 10^{-9}$, at least $4.85 \times 10^{-9}$, at least $4.80 \times 10^{-9}$, at least $4.75 \times 10^{-9}$, at least $4.70 \times 10^{-9}$, at least $4.65 \times 10^{-9}$, at least $4.60 \times 10^{-9}$, at least $4.55 \times 10^{-9}$, at least $4.5 \times 10^{-9}$, at least $4.45 \times 10^{-9}$, at least $4.40 \times 10^{-9}$, at least $4.35 \times 10^{-9}$, at least $4.30 \times 10^{-9}$, at least $4.25 \times 10^{-9}$, at least $4.20 \times 10^{-9}$, at least $4.15 \times 10^{-9}$, at least $4.10 \times 10^{-9}$, at least $4.05 \times 10^{-9}$, at least $4.0 \times 10^{-9}$, at least $3.95 \times 10^{-9}$, at least $3.90 \times 10^{-9}$, at least $3.85 \times 10^{-9}$, at least $3.80 \times 10^{-9}$, at least $3.75 \times 10^{-9}$, at least $3.70 \times 10^{-9}$, at least $3.65 \times 10^{-9}$, at least $3.60 \times 10^{-9}$9, at least $3.55 \times 10^{-9}$, at least $3.5 \times 10^{-9}$, at least $3.45 \times 10^{-9}$, at least $3.40 \times 10^{-9}$, at least $3.35 \times 10^{-9}$, at least $3.30 \times 10^{-9}$, at least $3.25 \times 10^{-9}$, at least $3.20 \times 10^{-9}$, at least $3.15 \times 10^{-9}$, at least $3.10 \times 10^{-9}$, at least $3.05 \times 10^{-9}$, at least $3.0 \times 10^{-9}$, at least $2.95 \times 10^{-9}$, at least $2.90 \times 10^{-9}$, at least $2.85 \times 10^{-9}$, at least $2.80 \times 10^{-9}$, at least $2.75 \times 10^{-9}$, at least $2.70 \times 10^{-9}$, at least $2.65 \times 10^{-9}$, at least $2.60 \times 10^{-9}$, at least $2.55 \times 10^{-9}$, at least $2.5 \times 10^{-9}$, at least $2.45 \times 10^{-9}$, at least $2.40 \times 10^{-9}$, at least $2.35 \times 10^{-9}$, at least $2.30 \times 10^{-9}$, at least $2.25 \times 10^{-9}$, at least $2.20 \times 10^{-9}$, at least $2.15 \times 10^{-9}$, at least $2.10 \times 10^{-9}$, at least $2.05 \times 10^{-9}$, at least $2.0 \times 10^{-9}$9, at least $1.95 \times 10^{-9}$, at least $1.90 \times 10^{-9}$, at least $1.85 \times 10^{-9}$, at least $1.80 \times 10^{-9}$, at least $1.75 \times 10^{-9}$, at least $1.70 \times 10^{-9}$, at least $1.65 \times 10^{-9}$, at least $1.60 \times 10^{-9}$, at least $1.55 \times 10^{-9}$, at least $1.5 \times 10^{-9}$, at least $1.45 \times 10^{-9}$, at least $1.40 \times 10^{-9}$, at least $1.35 \times 10^{-9}$, at least $1.30 \times 10^{-9}$, at least $1.25 \times 10^{-9}$, at least $1.20 \times 10^{-9}$, at least $1.15 \times 10^{-9}$, at least $1.10 \times 10^{-9}$, at least $1.05 \times 10^{-9}$, at least $1.0 \times 10^{-9}$, at least $0.95 \times 10^{-9}$, at least $0.90 \times 10^{-9}$, at least $0.85 \times 10^{-9}$, at least $0.80 \times 10^{-9}$, at least $0.75 \times 10^{-9}$, at least $0.70 \times 10^{-9}$, at least $0.65 \times 10^{-9}$, at least $0.60 \times 10^{-9}$, at least $0.55 \times 10^{-9}$, at least $0.5 \times 10^{-9}$, at least $0.45 \times 10^{-9}$, at least $0.40 \times 10^{-9}$, at least $0.35 \times 10^{-9}$, at least $0.30 \times 10^{-9}$, at least $0.25 \times 10^{-9}$, at least $0.20 \times 10^{-9}$, at least $0.15 \times 10^{-9}$, at least $0.10 \times 10^{-9}$, at least $0.05 \times 10^{-9}$, at least $9.5 \times 10^{-10}$, at least $9.0 \times 10^{-10}$, at least $8.5 \times 10^{-10}$, at least $8.0 \times 10^{-10}$, or any value in between. For example, the disclosed methods can comprise anti-PD-L1 antibodies and functional fragments thereof having $K_D$ values of $8.2 \times 10^{-10}$, $2.31 \times 10^{-09}$, $8.24 \times 10^{-09}$, $3.25 \times 10^{-09}$, $3.46 \times 10^{-09}$, $1.91 \times 10^{-09}$, $7.97 \times 10^{-08}$, $2.41 \times 10^{-08}$, $9.5 \times 10^{-10}$, or $8.6 \times 10^{-10}$.

Likewise, the disclosed methods can comprise anti-PD-L1 antibodies and functional fragments thereof having $IC_{50}$ values between $4.0 \times 10^{-5}$ µg/ml and $9.5 \times 10^{-7}$ µg/ml or any value in between. For example, the disclosed methods can comprise anti-PD-L1 antibodies and functional fragments thereof having $IC_{50}$ values of $9.19 \times 10^{-7}$, $4.156 \times 10^{-5}$, $9.985 \times 10^{-7}$, $1.037 \times 10^{-6}$, or $3.463 \times 10^{-6}$.

In some embodiments, an immune response potentiating modality can comprise an anti-GITR antibody, an anti-OX40 antibody, an anti-CD137 antibody, a TLR agonist, or anti-CD40 antibody.

In some embodiments, a tumor-targeting antibody can comprise an anti-CAIX antibody, an anti-BCMA, an anti-CS-1, an anti-CD20 (e.g. Ublituximab), an anti-Her2, an anti-PCSA, or an anti-FcRL5.

In some embodiments, a small molecule drug can comprise a tumor-targeting small molecule drug, or, for instance, a BTK inhibitor (e.g. ibrutinib), an EGFR inhibitor (e.g. CK-101), a BET inhibitor (e.g. CK-103), a PARP inhibitor (e.g. olaparib or CK-102), a PI3Kdelta inhibitor (e.g. TGR-1202), or a BRAF inhibitor (e.g. Vemurafenib).

Particular treatment regimens may be evaluated according to whether it will improve a given patient's outcome, meaning it will reduce the risk of recurrence or increase the likelihood of progression-free survival of the given cancer.

Thus, for the purposes of this disclosure, a subject is treated if one or more beneficial or desired results, including desirable clinical results, are obtained. For example, beneficial or desired clinical results include, but are not limited to, one or more of the following: decreasing one or more symptoms resulting from the disease, increasing the quality of life of those suffering from the disease, decreasing the dose of other medications required to treat the disease, delaying the progression of the disease, and/or prolonging survival of individuals.

Furthermore, while the subject of the methods is generally a cancer patient, the age of the patient is not limited. The disclosed methods are useful for treating cancer, malignant disease, or cancer cell proliferation with various recurrence and prognostic outcomes across all age groups and cohorts. Thus, in some embodiments, the subject may be a pediatric subject, while in other embodiments, the subject may be an adult subject.

The following examples are given to illustrate the present invention. It should be understood, however, that the invention is not to be limited to the specific conditions or details described in these examples.

EXAMPLES

Example 1—Treatment of a Cancer Patient with the Disclosed Anti-PD-L1 Antibodies This example illustrates methods using anti-PD-L1 antibodies in the treatment of cancer.

A patient known to have or suspected of having cancer is administered a therapeutically effective amount of a pharmaceutical composition comprising an anti-PD-L1 antibody, by intravenous or subcutaneous injection. The patient is evaluated for the presence and/or severity of signs and symptoms associated with cancer, including, but not limited to, pain, weakness, etc., and the patient is treated until one or more signs/symptoms is reduced, ameliorated, or eliminated. Optionally, samples may be taken from the patient to monitor cancer progression following treatment. Optionally, another dose of the pharmaceutical composition is administered if signs/symptoms persist and/or if the cancer progresses or recurs.

Example 2—Production of Optimized Antibodies

Antigens were biotinylated using the EZ-Link Sulfo-NHS-Biotinylation Kit from Pierce. Goat anti-human F(ab')2 kappa-FITC (LC-FITC), Extravidin-PE (EA-PE) and streptavidin-633 (SA-633) were obtained from Southern Biotech, Sigma and Molecular Probes, respectively. Streptavidin MicroBeads and MACS LC separation columns were purchased from Miltenyi Biotec.

Affinity Maturation

Binding optimization of naïve clones was carried out utilizing three maturation strategies: diversification of VH CDRH1/CDRH2, PCR mutagenesis of the VH gene and VH mutagenesis with a focus on CDRH3.

CTI-07 Lineage

The first cycle of optimization focused on selection of improved binders from a library in which the CTI-07 VH gene was diversified by mutagenic PCR using techniques known in the art. Round 1: Selections were performed by presenting VH mutated forms of the full-length CTI-07 IgG on the surface of yeast. These libraries were incubated with 100 nM biotinylated PD-L1, then detecting IgG expression by an anti-LC FITC reagent (IgG expression) and SA-633 (detection of antigen binding) and viable cells by propidium iodine staining. The top antigen binding/IgG expressing cells were selected by FACS. Round 2: Selections were performed as per Round 1, but using 10 nM biotinylated PD-L1 for discrimination of antigen binding. Round 3: Library expression was carried out as per Rounds 1 &2. Round 3 employed the use of a poly-specificity reagent (PSR) to remove non-specific antibodies from the selection output (Y. Xu et. al., "Addressing Polyspecificity of Antibodies Selected from an in vitro Yeast Presentation System: a FACS-based, High-Throughput Selection and Analytical Tool." PEDS 26.10 (2013): 663-70.) These libraries were incubated with 1:10 dilution of biotinylated PSR reagent, IgG expression was detected by an anti-LC FITC reagent (IgG expression) and PSR binding was detected by EA-PE (detection of antigen binding) and viable cells by propidium iodine staining. The top 1-2% of IgG positive, PSR negative, PI negative cells were sorted and carried to Round 4. Round 4: Selections were performed as per Round 2, but using 1 nM biotinylated PD-L1 for discrimination of antigen binding. Top clones were plated, and sequenced to determine unique IgG sequences. Unique IgG sequences were submitted for antibody production, purification and characterization.

The second cycle of optimization focused on the selection of improved binders from a library in which the VH gene was diversified by mutagenic PCR while also utilizing degenerate CDRH3 oligos to increase the mutagenic rate within CDRH3. This amplification technique was performed using techniques well known in the art. Round 1: Selections were performed by presenting VH mutated forms of the full-length parent IgG on the surface of yeast. These libraries were incubated with 10 nM biotinylated PD-L1, then detecting IgG expression by an anti-LC FITC reagent (IgG expression) and SA-633 (detection of antigen binding) and viable cells by propidium iodine staining. The top antigen binding/IgG expressing cells were selected by FACS. Round 2: Selections were performed as per Round 1, but using 2 nM biotinylated PD-L1 for discrimination of antigen binding. Top clones were plated, and sequenced to determine unique IgG sequences. Unique IgG sequences were submitted for antibody production, purification and characterization.

CTI-09 Lineage

CTI-09 optimization employed the use of CDRH1 and CDRH2 variegation: The CDRH3 of CTI-09 was amplified by PCR and then recombined into a premade vector library with CDRH1 and CDRH2 variants of a diversity of 1×108. Round 1: Selections were performed by presenting VH mutated forms of the full-length CTI-09 IgG on the surface of yeast. These libraries were incubated with 100 nM biotinylated PD-L1. Antigen positive cells were selected by magnetic separation via the Miltenyi MACS system. In short libraries incubated with b-PD-L1 were incubated with streptavidin magnetic beads. Yeast/bead complexes were captured on a MACS LS column, with unlabeled cells passing into the waste. b-PD-L1 binding cells were then eluted into media for propagation for Round 2 of the selection process. Round 2: Selections were performed by presenting VH mutated forms of the full-length CTI-07 IgG on the surface of yeast. These libraries were incubated with 20 nM biotinylated PD-L1, then detecting IgG expression by an anti-LC FITC reagent (IgG expression) and SA-633 (detection of antigen binding) and viable cells by propidium iodine staining. The top antigen binding/IgG expressing cells were selected by FACS. Round 3: Library expression was carried out as per Rounds 1&2. Round 3 employed the use of a poly-specificity reagent (PSR) to remove non-specific antibodies from the selection output (Y. Xu et. al., "Addressing Polyspecificity of Antibodies Selected from an in vitro Yeast Presentation System: a FACS-based. High-Throughput Selection and Analytical Tool." PEDS 26.10 (2013): 663-70.) These libraries were incubated with 1:10 dilution of biotinylated PSR reagent, IgG expression was detected by an anti-LC FITC reagent (IgG expression) and PSR binding was detected by EA-PE (detection of antigen binding) and viable cells by propidium iodine staining. The top 1-2% of IgG positive, PSR negative, PI negative cells were sorted and carried to Round 4. Round 4: The induced Round 3 output was incubated with 20 nM b-PD-L1. Cells were pelleted and washed to remove any remaining b-PD-L1. This cell pellet was resuspended in 1 uM unlabeled PD-L1. Top antigen binders were discriminated by their ability to retain b-PD-L1 antigen over time. Top clones were plated, and sequenced to determine unique IgG sequences. Unique IgG sequences were submitted for antibody production, purification and characterization.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences).

Example 3—Competitive FACS with PD-L1 Antibodies

Chinese hamster ovary (CHO) cells were transfected with a PD-L1 expression vector and subsequently selected for expression of the protein (PD-L+ cells). The CHO cells were incubated with 1 µg/ml biotin-labeled PD-1 for 1 hour.

Following incubation with biotin-labeled PD-1, anti-PD-L1 antibodies were added to the supernatant at 4-fold dilutions, starting at 10 µm/ml, and allowed to incubate for 1 hour. The cells were washed and then contacted with streptavidin-PE. Streptavidin-PE staining was analyzed by flow cytometry to determine percent inhibition of PD-1 binding by the anti-PD-L1 antibodies.

TABLE 3

|  | Clinical Control mAb | CTI-09 | CTI-48 | CTI-50 | CTI-58 |
| --- | --- | --- | --- | --- | --- |
| $IC_{50}$, g/ml | 9.19e–007 | 4.156e–005 | 9.985e–007 | 1.037e–006 | 3.463e–006 |

$IC_{50}$ values for several antibodies, including Clinical Control mAb (as defined by the VH domain represented by SEQ ID NO: 73 and the VL domain represented by SEQ ID NO: 74), CTI-09, CTI-48, CTI-50, and CTI-58 were calculated and can be found in Table 3. FIG. 1 shows the results of this study.

Example 4—Antibody Binding Kinetics, Specificity, and Selectivity

Octet data analysis was used in determining affinity measurements to assess antibody binding kinetics. 2 mL of the loading sample was prepared at 20 ug/mL (default concentration) in kinetic buffer. Aliquot at least 200 uL into a black 96-well plate. Concentration ranges for the sample were based on the estimated $K_D$ of the interaction (if available). Generally, the serial dilution was in a range from 0.1 $K_D$ to 10 $K_D$. A 7-point dilution was made into the sample column using kinetic buffer as the sample diluent. The last well of the sample column was used as a reference well later in data analysis, should only contain kinetic buffer.

Biosensors were hydrated in kinetic buffer (1×PBS, 0.1% BSA, 0.02% Tween20, 0.05% Sodium Azide) at room temperature for 10 minutes.

TABLE 4

| Sample ID | Loading Sample ID | KD (M) | kon(1/Ms) | kdis (1/s) |
|---|---|---|---|---|
| huPDL1 | CTI-48 | 8.47E−10 | 7.20E+05 | 6.10E−04 |
| msPDL1 | CTI-48 | N/A | N/A | N/A |
| cynoPDL1 | CTI-48 | 5.55E−10 | 1.14E+06 | 6.35E−04 |

Figure 2:
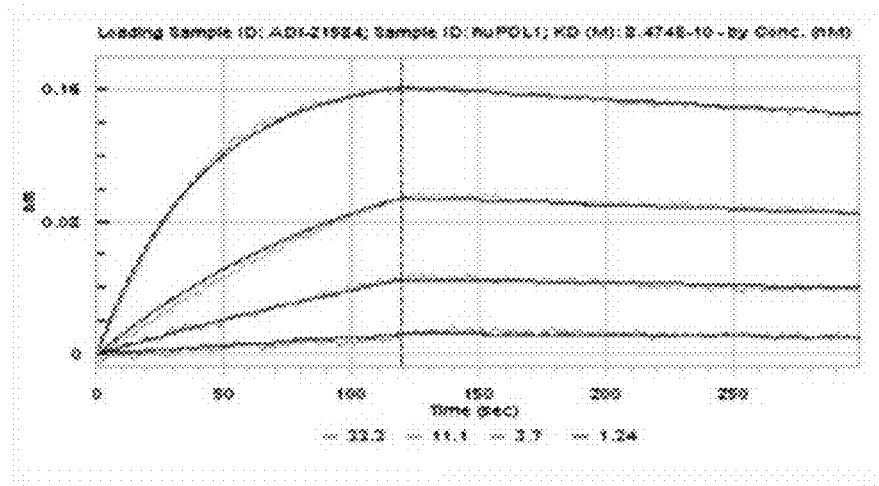
FIG. 2 shows the binding kinetics of exemplary anti-PD-L1 antibody CTI-48 against (A) human PD-L, (B) mouse PD-L1, and (C) cyno PD-L1.
Figure 2:
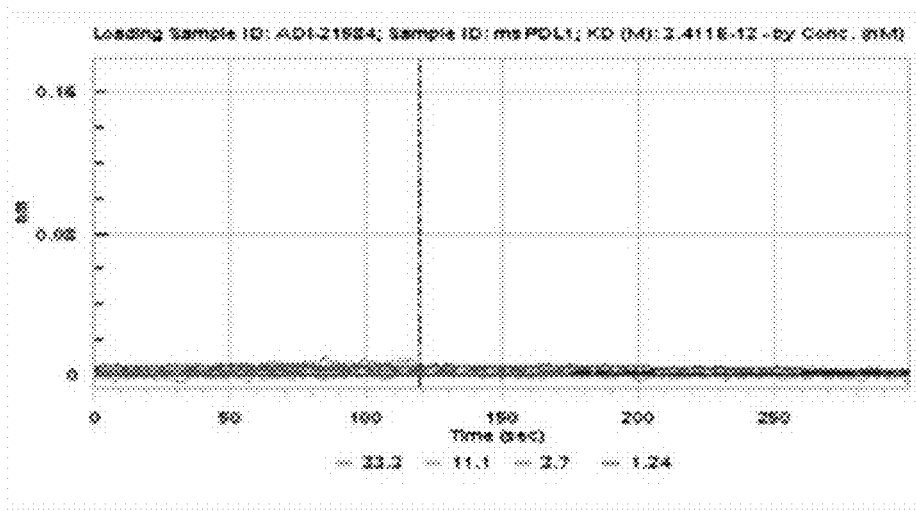

Kinetic values for one exemplary anti-PD-L1 antibody, CTI-48, can be found in Table 4, and experimental results are shown in FIG. 2.

Example 5—Antibody Binding Affinity

ForteBio affinity measurements were performed generally as previously described (see, e.g., Estep et al., 2013). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 5 minutes, afterwards they were transferred to assay buffer for 5 min for off-rate measurement. Kinetics were analyzed using the 1:1 binding model.

TABLE 5

| Ab Name | VH CDR3 Lineage | IgG $K_D$ (M) monovalent | kon (1/Ms) | koff (1/s) |
|---|---|---|---|---|
| CTI-09 | 1 | N.B. | | |
| CTI-48 | 1 | 8.24E−10 | 7.68E+05 | 6.33E−04 |
| CTI-49 | 1 | 2.31E−09 | 7.28E+05 | 1.68E−03 |
| CTI-76 | 1 | 8.24E−09 | 6.62E+05 | 5.45E−03 |
| CTI-77 | 1 | 3.25E−09 | 5.44E+05 | 1.77E−03 |
| CTI-78 | 1 | 3.46E−09 | 6.18E+05 | 2.14E−03 |
| CTI-50 | 1 | 1.91E−09 | 7.94E+05 | 1.52E−03 |
| CTI-07 | 2 | 7.97E−08 | 4.92E+05 | 3.92E−02 |
| CTI-58 | 2 | 2.41E−08 | 4.61E+05 | 1.11E−02 |
| Clinical Control mAb | NA | 9.5E−10 | | |
| CTI-57 | 2 | 8.6E−10 | 5.2E+05 | 4.5E−04 |
| CTI-97 | 1 | 1.82E−09 | 5.11E+05 | 9.28E−04 |
| CTI-98 | 1 | 1.70E−09 | 5.02E+05 | 8.52E−04 |

Binding values for several exemplary antibodies are shown in Table 5.

Example 6—ADCC Activity of Anti-PD-L1 Antibodies

Reporter bioassays were performed in order to determine antibody-dependent cell-mediates cytotoxicity (ADCC) of the disclosed anti-PD-L1 antibodies. The assays utilized SUDHL-1 lymphoma cells and donor PBMCs. Various antibodies were tested at concentrations of 1 or 3 ug/ml.

Figure 3:
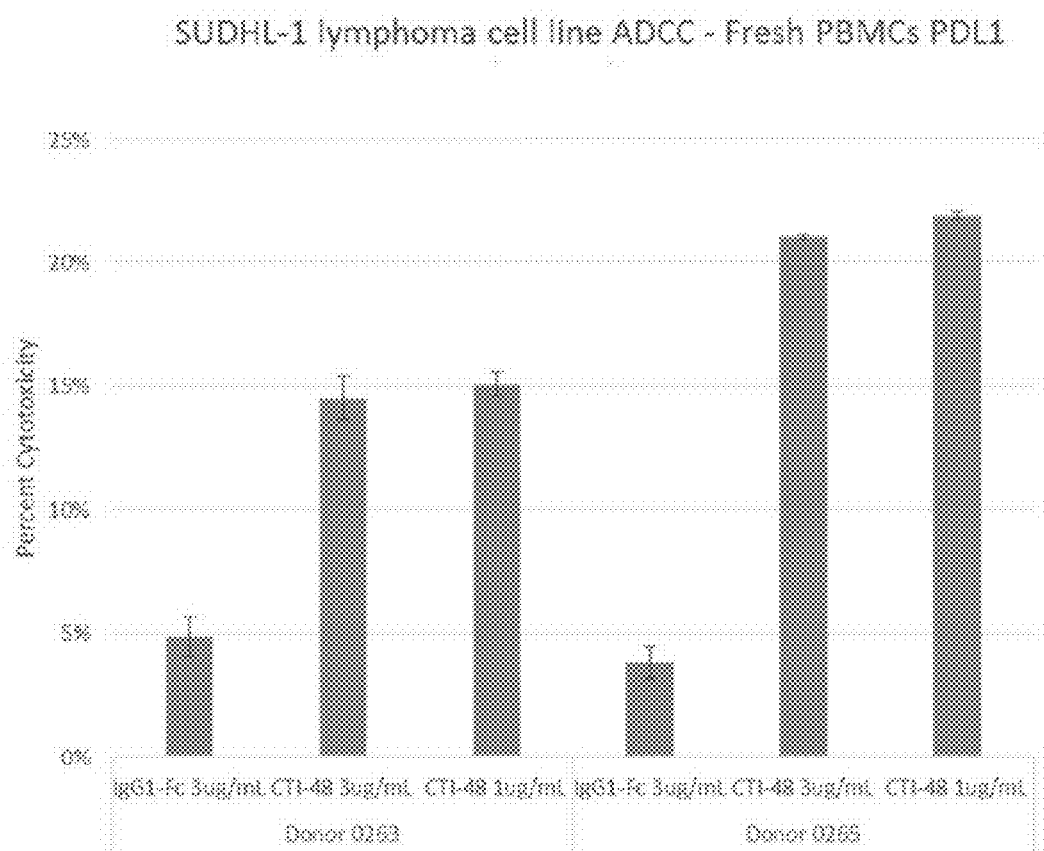
FIG. 3 shows that exemplary anti-PD-L1 antibody CTI-48 exhibits ADCC activity on PD-L+ lymphoma cells with primary NK cells.
Figure 4:
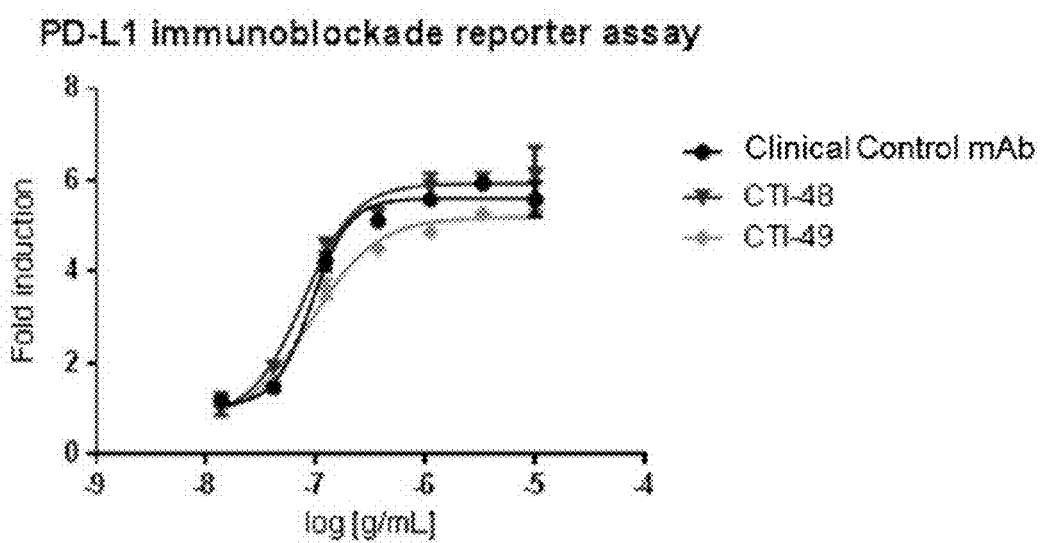
FIG. 4 shows reversal of T-cell inhibition with PD-L1 in a reporter (NFAT) bioassay of immunoblockade with select anti-PD-L1 antibodies.

The results of this study, which are shown for exemplary anti-PD-L1 antibody CTI-48 in FIG. 3, are represented by percent cytotoxicity following a 4 hour incubation with the disclosed antibodies.

Example 7—Immunoblockade Reporter Assay

Immunoblockade assays were performed using a PD1/PD-L1 Blockade Assay Kit (Promega, CS187111) in 96 well plates. Three major events occur in the assay. Event 1: TCR-mediated NFAT activation occurs when engineered Jurkat PD-1 Effector cells and aAPC (artificial antigen presenting cell) PD-L1 cells are engaged through TCR/TCR activator interaction. Event 2: Inhibition of NFAT signal by PD-1:PD-L1 ligation when no blocking antibodies are present. Event 3: Recovery of NFAT signal by addition of anti-PD-1 or anti-PD-L1 blocking antibody.

The day before assay, 25 mL of cell recovery medium (10% FBS/F-12) was made in 50 mL conical tubes for Thaw-and-Use PD-L1 cells by adding 2.5 mL FBS to 22.5 mL F-12. One vial of Thaw-and-Use PD-L1 cells (CS187103) was removed from freezer storage and transferred to the bench on dry ice. The viral was thawed in a 37° C. water bath until cells are just thawed (about 3-4 minutes). The cell suspension was gently mixed in the vial by pipetting up and down, and transfer all the cells (0.5 mL) to the tube labeled "PD-L1 cells" containing 14.5 mL cell recovery medium followed by gentle inversions. The cell suspension was transferred to a sterile reagent reservoir. Immediately, using a multichannel pipette, and 100 µL of cell recovery medium was added per well to outside wells for assay plates. The plates were incubated overnight in a CO2 incubator at 37° C.

On the day of assay, fresh assay buffer (RPMI 1640+1% FBS) was prepared, and seven-point three-fold serial dilutions were made in assay buffer for each of the test antibodies at 2× of final concentration. 95 µL of medium was removed from all the wells on the assay plates, and 40 µL of serial dilutions of the test antibodies was added to the wells containing PD-L1 cells. 80 µL per well assay buffer was added to the outside wells for each plate.

Thaw-and-Use PD-1 Effector cells (CS187105) were transferred into the assay plates, and the plates were incubated for six hours at 37° C. in CO2 incubator. After the six-hour induction, the assay plates were removed from the CO2 incubator and equilibrated at ambient temperature for 5-10 min. 80 µL of Bio-Glo™ Reagent was added to every test well, and the plates were incubated for another 5-10 min at ambient temperature. Luminescence was measured in POLARstar Omega plate reader with 0.5 sec integration.

The following antibodies were tested with final concentrations of 10 µg/mL, 3.33 µg/mL, 1.11 µg/mL, 0.37 µg/mL, 0.123 µg/mL, 0.041 µg/mL, and 0.014 µg/mL: CTI-2, Clinical Control mAb, CTI-09, CTI-48, CTI-50, CTI-07, and CTI-58.

Results for exemplary antibodies including Clinical Control mAb, CTI-48, and CTI-49 are shown in Table 6 below.

TABLE 6

| | Clinical Control mAb | CTI-48 | CTI-49 |
|---|---|---|---|
| $EC_{50}$, g/mL | 9.213e−008 | 7.750e−008 | 9.191e−008 |

Example 8—PD-L1/B7.1 Inhibitor Screening Assay

A commercially available assay kit was used to screen and profile the interaction of the disclosed antibodies and the PD-L1/B7.1 interaction. The kit came in a 96-well format with biotin-labeled B7-1 (CD80), purified PD-L1, streptavidin-labeled HRP, and assay buffer for 100 binding reactions. The kit was used to detect biotin-labeled B7.1 by streptavidin-HRP.

First, PD-L1 was coated on a 96-well plate. Next, either one of the disclosed antibodies, a positive control, a substrate control, or a blank was added to each well and incubated prior to the addition of B7.1-biotin. Finally, the plate is treated with streptavidin-HRP followed by addition of an HRP substrate to produce chemiluminescence, which can then be measured using a chemiluminescence reader.

The following antibodies were tested for their inhibitory effect on the binding of PD-L1 and B7.1 at concentrations of 30 µg/mL, 10 µg/mL, 3.33 µg/mL, 1.11 µg/mL, 0.37 µg/mL, and 0.123 µg/mL: CTI-1, CTI-2, CTI-33, CTI-48, and CTI-55.

Figure 5:
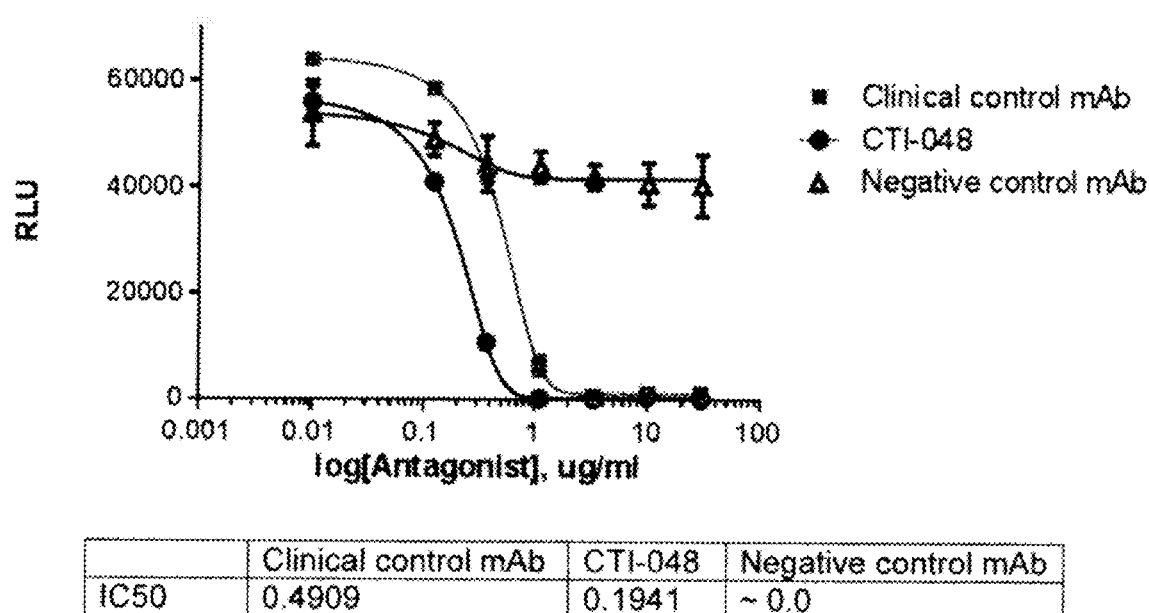
FIG. 5 shows blocking of PD-L1 binding to B7.1 by CTI-48 and a clinical control mAb.

Exemplary results indicate that the $IC_{50}$ for binding inhibition of the disclosed antibodies ranges between 0.1816 and 0.5056 µg/mL. For instance, the $IC_{50}$ of CTI-48 was calculated to be 0.1816 µg/mL. A comparison of the activity of CTI-48 and a clinical control mAb is shown in FIG. 5.

Example 9—Effect of Antibodies on IFN-γ Production

Figure 6:
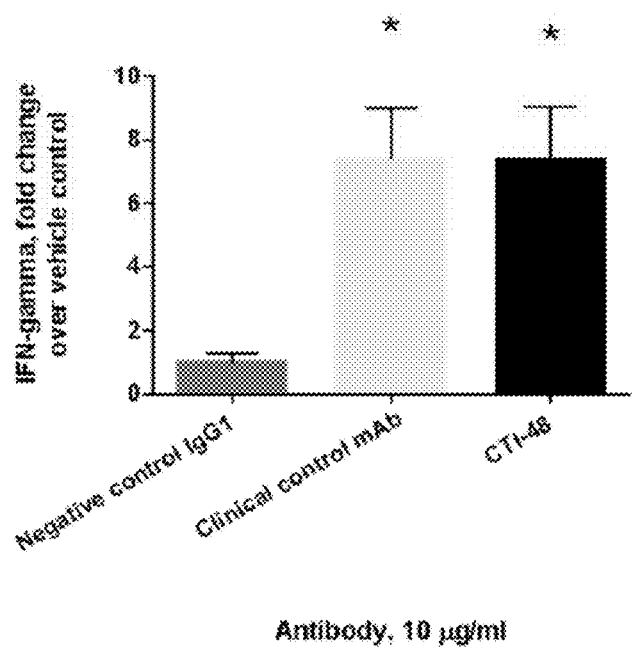
FIG. 6 shows the effect of the disclosed antibodies on IFN-γ production. Antibodies were dosed into mixed lymphocyte reaction (MLR) cultures at a concentration of 10 μg/mL. Data were normalized to vehicle control and are presented as combined mean+SEM (n=6). *p<0.05 p<0.01, *p<0.001 indicates statistical significance when compared to appropriate isotype control (hIgG1) using Ordinary one-way ANOVA with Dunnett's multiple comparison post-hoc test. This figure shows a side-by-side comparison of CTI-48 and a clinical control mAb.

Antibodies were dosed into mixed lymphocyte reaction (MLR) cultures in order to determine the effects of the disclosed antibodies on IFN-γ production. The fold change in production of IFN-7 was determined after a 4-day MLR culture with antibodies at a concentration of 10 µg/mL. Exemplary results, including those of an appropriate isotype control (hIgG1). As shown in FIG. 6, CTI-48 induced a comparable response to a clinical control mAb and many of the tested antibody elicited a statistically significant increase in IFN-γ production, including a roughly 10-fold increase by CTI-33 and CTI-55 over control levels.

All patents and publications mentioned in the specification are indicative of the levels of those of ordinary skill in the art to which the disclosure pertains. All patents and publications are herein incorporated by reference to the same extent as if each individual publication was specifically and individually indicated to be incorporated by reference.

Further, one skilled in the art readily appreciates that the present disclosure is well adapted to carry out the objects and obtain the ends and advantages mentioned, as well as those inherent therein. Modifications therein and other uses will occur to those skilled in the art. These modifications are encompassed within the spirit of the disclosure and are defined by the scope of the claims, which set forth non-limiting embodiments of the disclosure.

What is claimed:

1. An antibody or a fragment thereof that binds to human programmed death-ligand 1 (PD-L1), wherein the antibody or fragment thereof comprises:
  a heavy chain comprising: CDRH1 comprising amino acids 1-3 and 7-9 of SEQ ID NO: 1, wherein amino acids 4-6 are not SSY; CDRH2 comprising amino acids 9-17 of SEQ ID NO: 8; and CDRH3 comprising SEQ ID NO: 15; and
  a light chain comprising CDRL1 comprising SEQ ID NO: 20; CDRL2 comprising SEQ ID NO: 21; and CDRL3 comprising SEQ ID NO: 22, SEQ ID NO: 75, or SEQ ID NO: 76.

2. The antibody or fragment thereof according to claim 1, wherein the CDRH1 region comprises an amino acid sequence selected from the group consisting of SEQ ID NOS: 2, 3, 4, 5, 6 and 7.

3. The antibody or fragment thereof according to claim 1, wherein the CDRH2 region comprises an amino acid sequence selected from the group consisting of SEQ ID NOS: 8, 9, 10, 11, 12, 13 and 14.

4. The antibody or fragment thereof according to claim 1, wherein the variable heavy framework region 1 comprises SEQ ID NO. 26.

5. The antibody or fragment thereof according to claim 1, wherein the variable heavy framework region 1 comprises SEQ ID NO. 27.

6. The antibody or fragment thereof according to claim 1, wherein the variable heavy framework region 2 comprises SEQ ID NO. 28.

7. The antibody or fragment thereof according to claim 1, wherein the variable heavy framework region 3 comprises SEQ ID NO. 29.

8. The antibody or fragment thereof according to claim 1, wherein the variable heavy framework region 4 comprises SEQ ID NO. 30.

9. The antibody or fragment thereof according to claim 1, wherein the variable light framework region 1 comprises SEQ ID NO. 31.

10. The antibody or fragment thereof according to claim 1, wherein the variable light framework region 2 comprises SEQ ID NO. 32.

11. The antibody or fragment thereof according to claim 1, wherein the variable light framework region 3 comprises SEQ ID NO. 33, SEQ ID NO. 77, or SEQ ID NO. 78.

12. The antibody or fragment thereof according to claim 1, wherein the variable light framework region 4 comprises SEQ ID NO. 34.

13. The antibody or fragment thereof according to claim 1, wherein the variable heavy chain sequence comprises an amino acid sequence selected from the group consisting of SEQ ID NOS: 36, 37, 38, 39, 40 and 41.

14. The antibody or fragment thereof according to claim 1, wherein the variable heavy chain sequence comprises an amino acid sequence selected from the group consisting of SEQ ID NOS: 51, 52, 53, 54, 55 and 56.

15. The antibody or fragment thereof according to claim 1, wherein the variable light chain sequence comprises SEQ ID NO: 42.

16. A pharmaceutical composition comprising the antibody or fragment thereof according to claim 1.

17. An antibody or a fragment thereof that binds to human programmed death-ligand 1 (PD-L1), wherein the antibody or fragment thereof comprises a heavy chain comprising SEQ ID NO: 35.

18. A method of inhibiting cancer cell proliferation in a subject, comprising administering an antibody or fragment that binds human PD-L1 with a $K_D$ of at least $8.30 \times 10^{-9}$; a CDRH2 comprising SEQ ID NO: 9, 10, 11, 12, 13, or 14; and CDRH3 comprising SEQ ID NO: 15 to a subject with cancer.

19. The method of claim 18, wherein the cancer is a hematological cancer, a neurological cancer, breast cancer, a gastrointestinal cancer, renal cell carcinoma, or a genitourinary cancer.

20. The method of claim 18, wherein the method further comprises a step of administering to the subject an additional therapeutic compound.

21. The method of claim 20, wherein the additional therapeutic compound is a CAR-T cell, a tumor-targeting antibody, an immune response potentiating modality, or a small molecule drug.

22. A method of inhibiting tumor cell proliferation in a subject, comprising administering an antibody or fragment thereof that binds human PD-L1 with a $K_D$ of at least $2.50 \times 10^{-8}$ and CDRH3 comprising amino acids 6-13 of SEQ ID NO: 18 to a subject with cancer.

23. The method of claim 22, wherein the method further comprises a step of administering to the subject an additional therapeutic compound.

24. The method of claim 23, wherein the additional therapeutic compound is a CAR-T cell, a tumor-targeting antibody, an immune response potentiating modality, or a small molecule drug.

25. The method of claim 18, wherein the antibody or fragment that binds human PD-L1 comprises a CDRH1 comprising SEQ ID NO: 2, 3, 4, 5, 6, or 7.

26. The method of claim 25, wherein the antibody or fragment that binds human PD-L1 comprises a CDRL1 comprising SEQ ID NO: 20, a CDRL2 comprising SEQ ID NO: 21, and a CDRL3 comprising SEQ ID NO: 22.

27. The method of claim 25, wherein the antibody or fragment that binds human PD-L1 comprises a CDRL1 comprising SEQ ID NO: 20, a CDRL2 comprising SEQ ID NO: 21, and a CDRL3 comprising SEQ ID NO: 75 or 76.

28. The method of claim 22, wherein the antibody or fragment that binds human PD-L1 comprises a CDRH1 comprising SEQ ID NO: 16 and a CDRH2 comprising SEQ ID NO: 17.

29. The method of claim 28, wherein the antibody or fragment that binds human PD-L1 comprises a CDRL1 comprising SEQ ID NO: 23, a CDRL2 comprising SEQ ID NO: 24, and a CDRL3 comprising SEQ ID NO: 25.

30. A method of treatment, comprising administering to a subject with cancer an anti-PD-L1 antibody comprising:
(i) a heavy chain comprising a CDRH1 comprising SEQ ID NO: 2, a CDRH2 comprising SEQ ID NO: 9, and a CDRH3 comprising SEQ ID NO: 15; and a light chain comprising a CDRL1 comprising SEQ ID NO: 20, a CDRL2 comprising SEQ ID NO: 21, and a CDRL3 comprising SEQ ID NO: 22;
(ii) a heavy chain comprising a CDRH1 comprising SEQ ID NO: 3, a CDRH2 comprising SEQ ID NO: 10, and a CDRH3 comprising SEQ ID NO: 15; and a light chain comprising a CDRL1 comprising SEQ ID NO: 20, a CDRL2 comprising SEQ ID NO: 21, and a CDRL3 comprising SEQ ID NO: 22;
(iii) a heavy chain comprising a CDRH1 comprising SEQ ID NO: 4, a CDRH2 comprising SEQ ID NO: 11, and a CDRH3 comprising SEQ ID NO: 15; and a light chain comprising a CDRL1 comprising SEQ ID NO: 20, a CDRL2 comprising SEQ ID NO: 21, and a CDRL3 comprising SEQ ID NO: 22;
(iv) a heavy chain comprising a CDRH1 comprising SEQ ID NO: 5, a CDRH2 comprising SEQ ID NO: 12, and a CDRH3 comprising SEQ ID NO: 15; and a light chain comprising a CDRL1 comprising SEQ ID NO: 20, a CDRL2 comprising SEQ ID NO: 21, and a CDRL3 comprising SEQ ID NO: 22;
(v) a heavy chain comprising a CDRH1 comprising SEQ ID NO: 6, a CDRH2 comprising SEQ ID NO: 13, and a CDRH3 comprising SEQ ID NO: 15; and a light chain comprising a CDRL1 comprising SEQ ID NO: 20, a CDRL2 comprising SEQ ID NO: 21, and a CDRL3 comprising SEQ ID NO: 22;
(vi) a heavy chain comprising a CDRH1 comprising SEQ ID NO: 7, a CDRH2 comprising SEQ ID NO: 14, and a CDRH3 comprising SEQ ID NO: 15; and a light chain comprising a CDRL1 comprising SEQ ID NO: 20, a CDRL2 comprising SEQ ID NO: 21, and a CDRL3 comprising SEQ ID NO: 22;
(vii) a heavy chain comprising a CDRH1 comprising SEQ ID NO: 2, a CDRH2 comprising SEQ ID NO: 9, and a CDRH3 comprising SEQ ID NO: 15; and a light chain comprising a CDRL1 comprising SEQ ID NO: 20, a CDRL2 comprising SEQ ID NO: 21, and a CDRL3 comprising SEQ ID NO: 75; or
(viii) a heavy chain comprising a CDRH1 comprising SEQ ID NO: 2, a CDRH2 comprising SEQ ID NO: 9, and a CDRH3 comprising SEQ ID NO: 15; and a light chain comprising a CDRL1 comprising SEQ ID NO: 20, a CDRL2 comprising SEQ ID NO: 21, and a CDRL3 comprising SEQ ID NO: 76.

31. A method of treatment, comprising administering to a subject with cancer an anti-PD-L1 antibody comprising:
(i) a heavy chain comprising a CDRH1 comprising SEQ ID NO: 16, a CDRH2 comprising SEQ ID NO: 17, and a CDRH3 comprising SEQ ID NO: 18; and a light chain comprising a CDRL1 comprising SEQ ID NO: 23, a CDRL2 comprising SEQ ID NO: 24, and a CDRL3 comprising SEQ ID NO: 25; or
(ii) a heavy chain comprising a CDRH1 comprising SEQ ID NO: 16, a CDRH2 comprising SEQ ID NO: 17, and a CDRH3 comprising SEQ ID NO: 19; and a light chain comprising a CDRL1 comprising SEQ ID NO: 23, a CDRL2 comprising SEQ ID NO: 24, and a CDRL3 comprising SEQ ID NO: 25.

* * * * *

SEQUENCE LISTING

```
<160> NUMBER OF SEQ ID NOS: 78

<210> SEQ ID NO 1
<211> LENGTH: 9
<212> TYPE: PRT
<213> ORGANISM: Homo sapiens

<400> SEQUENCE: 1

Gly Thr Phe Ser Ser Tyr Ala Ile Ser
1               5

<210> SEQ ID NO 2
<211> LENGTH: 9
<212> TYPE: PRT
<213> ORGANISM: Homo sapiens

<400> SEQUENCE: 2

Gly Thr Phe Ser Arg Ser Ala Ile Ser
1               5

<210> SEQ ID NO 3
<211> LENGTH: 9
<212> TYPE: PRT
<213> ORGANISM: Homo sapiens

<400> SEQUENCE: 3

Gly Thr Phe Ser Gly Tyr Ala Ile Ser
1               5

<210> SEQ ID NO 4
<211> LENGTH: 9
<212> TYPE: PRT
<213> ORGANISM: Homo sapiens

<400> SEQUENCE: 4

Gly Thr Phe Trp Arg Tyr Ala Ile Ser
1               5

<210> SEQ ID NO 5
<211> LENGTH: 9
```

```
<212> TYPE: PRT
<213> ORGANISM: Homo sapiens

<400> SEQUENCE: 5

Gly Thr Phe Gly Ser Tyr Ala Ile Ser
1               5

<210> SEQ ID NO 6
<211> LENGTH: 9
<212> TYPE: PRT
<213> ORGANISM: Homo sapiens

<400> SEQUENCE: 6

Gly Thr Phe Gly Thr Tyr Ala Ile Ser
1               5

<210> SEQ ID NO 7
<211> LENGTH: 9
<212> TYPE: PRT
<213> ORGANISM: Homo sapiens

<400> SEQUENCE: 7

Gly Thr Phe Ser Pro Lys Ala Ile Ser
1               5

<210> SEQ ID NO 8
<211> LENGTH: 17
<212> TYPE: PRT
<213> ORGANISM: Homo sapiens

<400> SEQUENCE: 8

Gly Ile Ile Pro Ile Phe Gly Thr Ala Asn Tyr Ala Gln Lys Phe Gln
1               5                   10                  15

Gly

<210> SEQ ID NO 9
<211> LENGTH: 17
<212> TYPE: PRT
<213> ORGANISM: Homo sapiens

<400> SEQUENCE: 9

Val Ile Ile Pro Ala Phe Gly Glu Ala Asn Tyr Ala Gln Lys Phe Gln
1               5                   10                  15

Gly

<210> SEQ ID NO 10
<211> LENGTH: 17
<212> TYPE: PRT
<213> ORGANISM: Homo sapiens

<400> SEQUENCE: 10

Val Ile Ile Pro Ala Phe Gly Thr Ala Asn Tyr Ala Gln Lys Phe Gln
1               5                   10                  15

Gly

<210> SEQ ID NO 11
<211> LENGTH: 17
<212> TYPE: PRT
<213> ORGANISM: Homo sapiens

<400> SEQUENCE: 11

Val Ile Ile Pro Ile Trp Gly Lys Ala Asn Tyr Ala Gln Lys Phe Gln
1               5                   10                  15
```

Gly

<210> SEQ ID NO 12
<211> LENGTH: 17
<212> TYPE: PRT
<213> ORGANISM: Homo sapiens

<400> SEQUENCE: 12

Gly Ile Tyr Pro Ala Phe Gly Thr Ala Asn Tyr Ala Gln Lys Phe Gln
1               5                   10                  15

Gly

<210> SEQ ID NO 13
<211> LENGTH: 17
<212> TYPE: PRT
<213> ORGANISM: Homo sapiens

<400> SEQUENCE: 13

Gly Ile Tyr Pro Arg Phe Gly Thr Ala Asn Tyr Ala Gln Lys Phe Gln
1               5                   10                  15

Gly

<210> SEQ ID NO 14
<211> LENGTH: 17
<212> TYPE: PRT
<213> ORGANISM: Homo sapiens

<400> SEQUENCE: 14

Val Ile Ile Pro Ile Phe Gly Pro Ala Asn Tyr Ala Gln Lys Phe Gln
1               5                   10                  15

Gly

<210> SEQ ID NO 15
<211> LENGTH: 13
<212> TYPE: PRT
<213> ORGANISM: Homo sapiens

<400> SEQUENCE: 15

Ala Arg Gly Arg Gln Met Phe Gly Ala Gly Ile Asp Phe
1               5                   10

<210> SEQ ID NO 16
<211> LENGTH: 9
<212> TYPE: PRT
<213> ORGANISM: Homo sapiens

<400> SEQUENCE: 16

Tyr Thr Leu Ser Ser His Gly Ile Thr
1               5

<210> SEQ ID NO 17
<211> LENGTH: 17
<212> TYPE: PRT
<213> ORGANISM: Homo sapiens

<400> SEQUENCE: 17

Trp Ile Ser Ala His Ser Gly His Ala Ser Asn Ala Gln Lys Val Glu
1               5                   10                  15

Asp

<210> SEQ ID NO 18

```
<211> LENGTH: 13
<212> TYPE: PRT
<213> ORGANISM: Homo sapiens

<400> SEQUENCE: 18

Ala Arg Val Trp Arg Ala Leu Tyr His Gly Met Asp Val
1               5                   10

<210> SEQ ID NO 19
<211> LENGTH: 13
<212> TYPE: PRT
<213> ORGANISM: Homo sapiens

<400> SEQUENCE: 19

Ala Arg Val His Ala Ala Leu Tyr His Gly Met Asp Val
1               5                   10

<210> SEQ ID NO 20
<211> LENGTH: 13
<212> TYPE: PRT
<213> ORGANISM: Homo sapiens

<400> SEQUENCE: 20

Thr Arg Ser Ser Gly Ser Ile Asp Ser Asn Tyr Val Gln
1               5                   10

<210> SEQ ID NO 21
<211> LENGTH: 7
<212> TYPE: PRT
<213> ORGANISM: Homo sapiens

<400> SEQUENCE: 21

Glu Asp Asn Gln Arg Pro Ser
1               5

<210> SEQ ID NO 22
<211> LENGTH: 11
<212> TYPE: PRT
<213> ORGANISM: Homo sapiens

<400> SEQUENCE: 22

Gln Ser Tyr Asp Ser Asn Asn Arg His Val Ile
1               5                   10

<210> SEQ ID NO 23
<211> LENGTH: 11
<212> TYPE: PRT
<213> ORGANISM: Homo sapiens

<400> SEQUENCE: 23

Gly Gly Asn Asn Ile Gly Ser Lys Gly Val His
1               5                   10

<210> SEQ ID NO 24
<211> LENGTH: 7
<212> TYPE: PRT
<213> ORGANISM: Homo sapiens

<400> SEQUENCE: 24

Asp Asp Ser Asp Arg Pro Ser
1               5

<210> SEQ ID NO 25
<211> LENGTH: 11
<212> TYPE: PRT
```

```
<213> ORGANISM: Homo sapiens

<400> SEQUENCE: 25

Gln Val Trp Asp Ser Ser Asp His Trp Val
1               5                   10

<210> SEQ ID NO 26
<211> LENGTH: 26
<212> TYPE: PRT
<213> ORGANISM: Homo sapiens

<400> SEQUENCE: 26

Glu Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 27
<211> LENGTH: 26
<212> TYPE: PRT
<213> ORGANISM: Homo sapiens

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25

<210> SEQ ID NO 28
<211> LENGTH: 14
<212> TYPE: PRT
<213> ORGANISM: Homo sapiens

<400> SEQUENCE: 28

Trp Val Arg Gln Ala Pro Gly Gln Gly Leu Glu Trp Met Gly
1               5                   10

<210> SEQ ID NO 29
<211> LENGTH: 30
<212> TYPE: PRT
<213> ORGANISM: Homo sapiens

<400> SEQUENCE: 29

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 30
<211> LENGTH: 11
<212> TYPE: PRT
<213> ORGANISM: Homo sapiens

<400> SEQUENCE: 30

Trp Gly Gln Gly Thr Leu Val Thr Val Ser Ser
1               5                   10

<210> SEQ ID NO 31
<211> LENGTH: 22
<212> TYPE: PRT
<213> ORGANISM: Homo sapiens

<400> SEQUENCE: 31
```

```
Asn Phe Met Leu Thr Gln Pro His Ser Val Ser Glu Ser Pro Gly Lys
1               5                   10                  15

Thr Val Thr Ile Ser Cys
            20
```

<210> SEQ ID NO 32
<211> LENGTH: 15
<212> TYPE: PRT
<213> ORGANISM: Homo sapiens

<400> SEQUENCE: 32

```
Trp Tyr Gln Gln Arg Pro Gly Ser Ala Pro Thr Thr Val Ile Tyr
1               5                   10                  15
```

<210> SEQ ID NO 33
<211> LENGTH: 34
<212> TYPE: PRT
<213> ORGANISM: Homo sapiens

<400> SEQUENCE: 33

```
Gly Val Pro Asp Arg Phe Ser Gly Ser Ile Asp Ser Ser Asn Ser
1               5                   10                  15

Ala Ser Leu Thr Ile Ser Gly Leu Lys Thr Glu Asp Glu Ala Asp Tyr
            20                  25                  30

Tyr Cys
```

<210> SEQ ID NO 34
<211> LENGTH: 10
<212> TYPE: PRT
<213> ORGANISM: Homo sapiens

<400> SEQUENCE: 34

```
Phe Gly Gly Gly Thr Lys Leu Thr Val Leu
1               5                   10
```

<210> SEQ ID NO 35
<211> LENGTH: 120
<212> TYPE: PRT
<213> ORGANISM: Homo sapiens

<400> SEQUENCE: 35

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe Trp Gly Gln
            100                 105                 110

Gly Thr Leu Val Thr Val Ser Ser
            115                 120
```

<210> SEQ ID NO 36
<211> LENGTH: 120

```
<212> TYPE: PRT
<213> ORGANISM: Homo sapiens

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Ser
            20                  25                  30

Ala Ile Ser Trp Val Arg Gln Ala Pro Gly Gln Gly Leu Glu Trp Met
        35                  40                  45

Gly Val Ile Ile Pro Ala Phe Gly Glu Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe Trp Gly Gln
            100                 105                 110

Gly Thr Leu Val Thr Val Ser Ser
        115                 120

<210> SEQ ID NO 37
<211> LENGTH: 120
<212> TYPE: PRT
<213> ORGANISM: Homo sapiens

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly Tyr
            20                  25                  30

Ala Ile Ser Trp Val Arg Gln Ala Pro Gly Gln Gly Leu Glu Trp Met
        35                  40                  45

Gly Val Ile Ile Pro Ala Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe Trp Gly Gln
            100                 105                 110

Gly Thr Leu Val Thr Val Ser Ser
        115                 120

<210> SEQ ID NO 38
<211> LENGTH: 120
<212> TYPE: PRT
<213> ORGANISM: Homo sapiens

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Trp Arg Tyr
            20                  25                  30

Ala Ile Ser Trp Val Arg Gln Ala Pro Gly Gln Gly Leu Glu Trp Met
        35                  40                  45

Gly Val Ile Ile Pro Ile Trp Gly Lys Ala Asn Tyr Ala Gln Lys Phe
```

```
                    50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Gln Met Phe Gly Ala Gly Ile Asp Phe Trp Gly Gln
                100                 105                 110

Gly Thr Leu Val Thr Val Ser Ser
            115                 120

<210> SEQ ID NO 39
<211> LENGTH: 120
<212> TYPE: PRT
<213> ORGANISM: Homo sapiens

<400> SEQUENCE: 39

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Gly Ser Tyr
                20                  25                  30

Ala Ile Ser Trp Val Arg Gln Ala Pro Gly Gln Gly Leu Glu Trp Met
             35                  40                  45

Gly Gly Ile Tyr Pro Ala Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Gln Met Phe Gly Ala Gly Ile Asp Phe Trp Gly Gln
                100                 105                 110

Gly Thr Leu Val Thr Val Ser Ser
            115                 120

<210> SEQ ID NO 40
<211> LENGTH: 120
<212> TYPE: PRT
<213> ORGANISM: Homo sapiens

<400> SEQUENCE: 40

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Gly Thr Tyr
                20                  25                  30

Ala Ile Ser Trp Val Arg Gln Ala Pro Gly Gln Gly Leu Glu Trp Met
             35                  40                  45

Gly Gly Ile Tyr Pro Arg Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Gln Met Phe Gly Ala Gly Ile Asp Phe Trp Gly Gln
                100                 105                 110

Gly Thr Leu Val Thr Val Ser Ser
            115                 120
```

```
<210> SEQ ID NO 41
<211> LENGTH: 120
<212> TYPE: PRT
<213> ORGANISM: Homo sapiens

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Pro Lys
            20                  25                  30

Ala Ile Ser Trp Val Arg Gln Ala Pro Gly Gln Gly Leu Glu Trp Met
        35                  40                  45

Gly Val Ile Ile Pro Ile Phe Gly Pro Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe Trp Gly Gln
            100                 105                 110

Gly Thr Leu Val Thr Val Ser Ser
        115                 120

<210> SEQ ID NO 42
<211> LENGTH: 112
<212> TYPE: PRT
<213> ORGANISM: Homo sapiens

<400> SEQUENCE: 42

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Asp Ser Asn
            20                  25                  30

Tyr Val Gln Trp Tyr Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Arg His Val Ile Phe Gly Gly Gly Thr Lys Leu Thr Val Leu
            100                 105                 110

<210> SEQ ID NO 43
<211> LENGTH: 26
<212> TYPE: PRT
<213> ORGANISM: Homo sapiens

<400> SEQUENCE: 43

Glu Val Gln Leu Val Gln Ser Gly Gly Glu Val Lys Lys Pro Gly Ala
1               5                   10                  15

Ser Val Lys Val Ser Cys Lys Ala Ser Gly
            20                  25

<210> SEQ ID NO 44
<211> LENGTH: 30
<212> TYPE: PRT
<213> ORGANISM: Homo sapiens
```

```
<400> SEQUENCE: 44

Arg Val Thr Met Thr Thr Asp Thr Ser Thr Asn Thr Ala Tyr Met Glu
1               5                   10                  15

Leu Arg Ser Leu Thr Ala Asp Asp Thr Ala Val Tyr Tyr Cys
            20                  25                  30

<210> SEQ ID NO 45
<211> LENGTH: 22
<212> TYPE: PRT
<213> ORGANISM: Homo sapiens

<400> SEQUENCE: 45

Leu Ser Val Leu Thr Gln Pro Pro Ser Val Ser Val Ala Pro Gly Gln
1               5                   10                  15

Thr Ala Arg Ile Thr Cys
            20

<210> SEQ ID NO 46
<211> LENGTH: 15
<212> TYPE: PRT
<213> ORGANISM: Homo sapiens

<400> SEQUENCE: 46

Trp Tyr Gln Gln Lys Pro Gly Gln Ala Pro Val Leu Val Val Tyr
1               5                   10                  15

<210> SEQ ID NO 47
<211> LENGTH: 32
<212> TYPE: PRT
<213> ORGANISM: Homo sapiens

<400> SEQUENCE: 47

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 48
<211> LENGTH: 120
<212> TYPE: PRT
<213> ORGANISM: Homo sapiens

<400> SEQUENCE: 48

Glu Val Gln Leu Val Gln Ser Gly Gly Glu Val Lys Lys Pro Gly Ala
1               5                   10                  15

Ser Val Lys Val Ser Cys Lys Ala Ser Gly Tyr Thr Leu Ser Ser His
            20                  25                  30

Gly Ile Thr Trp Val Arg Gln Ala Pro Gly Gln Gly Leu Glu Trp Met
        35                  40                  45

Gly Trp Ile Ser Ala His Ser Gly His Ala Ser Asn Ala Gln Lys Val
    50                  55                  60

Glu Asp Arg Val Thr Met Thr Thr Asp Thr Ser Thr Asn Thr Ala Tyr
65                  70                  75                  80

Met Glu Leu Arg Ser Leu Thr Ala Asp Asp Thr Ala Val Tyr Tyr Cys
                85                  90                  95

Ala Arg Val Trp Arg Ala Leu Tyr His Gly Met Asp Val Trp Gly Gln
            100                 105                 110

Gly Thr Leu Val Thr Val Ser Ser
        115                 120
```

<210> SEQ ID NO 49
<211> LENGTH: 120
<212> TYPE: PRT
<213> ORGANISM: Homo sapiens

<400> SEQUENCE: 49

Glu Val Gln Leu Val Gln Ser Gly Gly Glu Val Lys Lys Pro Gly Ala
1               5                   10                  15

Ser Val Lys Val Ser Cys Lys Ala Ser Gly Tyr Thr Leu Ser Ser His
            20                  25                  30

Gly Ile Thr Trp Val Arg Gln Ala Pro Gly Gln Gly Leu Glu Trp Met
        35                  40                  45

Gly Trp Ile Ser Ala His Ser Gly His Ala Ser Asn Ala Gln Lys Val
    50                  55                  60

Glu Asp Arg Val Thr Met Thr Thr Asp Thr Ser Thr Asn Thr Ala Tyr
65                  70                  75                  80

Met Glu Leu Arg Ser Leu Thr Ala Asp Thr Ala Val Tyr Tyr Cys
                85                  90                  95

Ala Arg Val His Ala Ala Leu Tyr His Gly Met Asp Val Trp Gly Gln
            100                 105                 110

Gly Thr Leu Val Thr Val Ser Ser
        115                 120

<210> SEQ ID NO 50
<211> LENGTH: 108
<212> TYPE: PRT
<213> ORGANISM: Homo sapiens

<400> SEQUENCE: 50

Leu Ser Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Gly Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105

<210> SEQ ID NO 51
<211> LENGTH: 120
<212> TYPE: PRT
<213> ORGANISM: Homo sapiens

<400> SEQUENCE: 51

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Ser
            20                  25                  30

Ala Ile Ser Trp Val Arg Gln Ala Pro Gly Gln Gly Leu Glu Trp Met
        35                  40                  45

Gly Val Ile Ile Pro Ala Phe Gly Glu Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe Trp Gly Gln
                100                 105                 110

Gly Thr Leu Val Thr Val Ser Ser
        115                 120

<210> SEQ ID NO 52
<211> LENGTH: 120
<212> TYPE: PRT
<213> ORGANISM: Homo sapiens

<400> SEQUENCE: 52

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly Tyr
                20                  25                  30

Ala Ile Ser Trp Val Arg Gln Ala Pro Gly Gln Gly Leu Glu Trp Met
            35                  40                  45

Gly Val Ile Ile Pro Ala Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe Trp Gly Gln
                100                 105                 110

Gly Thr Leu Val Thr Val Ser Ser
        115                 120

<210> SEQ ID NO 53
<211> LENGTH: 120
<212> TYPE: PRT
<213> ORGANISM: Homo sapiens

<400> SEQUENCE: 53

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Trp Arg Tyr
                20                  25                  30

Ala Ile Ser Trp Val Arg Gln Ala Pro Gly Gln Gly Leu Glu Trp Met
            35                  40                  45

Gly Val Ile Ile Pro Ile Trp Gly Lys Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe Trp Gly Gln
                100                 105                 110

Gly Thr Leu Val Thr Val Ser Ser
        115                 120

<210> SEQ ID NO 54
<211> LENGTH: 120
<212> TYPE: PRT
<213> ORGANISM: Homo sapiens

<400> SEQUENCE: 54

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Ser Tyr
            20                  25                  30

Ala Ile Ser Trp Val Arg Gln Ala Pro Gly Gln Gly Leu Glu Trp Met
        35                  40                  45

Gly Gly Ile Tyr Pro Ala Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe Trp Gly Gln
            100                 105                 110

Gly Thr Leu Val Thr Val Ser Ser
        115                 120

<210> SEQ ID NO 55
<211> LENGTH: 120
<212> TYPE: PRT
<213> ORGANISM: Homo sapiens

<400> SEQUENCE: 55

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Thr Tyr
            20                  25                  30

Ala Ile Ser Trp Val Arg Gln Ala Pro Gly Gln Gly Leu Glu Trp Met
        35                  40                  45

Gly Gly Ile Tyr Pro Arg Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gln Met Phe Gly Ala Gly Ile Asp Phe Trp Gly Gln
            100                 105                 110

Gly Thr Leu Val Thr Val Ser Ser
        115                 120

<210> SEQ ID NO 56
<211> LENGTH: 120
<212> TYPE: PRT
<213> ORGANISM: Homo sapiens

<400> SEQUENCE: 56

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Pro Lys
            20                  25                  30

Ala Ile Ser Trp Val Arg Gln Ala Pro Gly Gln Gly Leu Glu Trp Met

```
                35                  40                  45
Gly Val Ile Ile Pro Ile Phe Gly Pro Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Gln Met Phe Gly Ala Gly Ile Asp Phe Trp Gly Gln
            100                 105                 110

Gly Thr Leu Val Thr Val Ser Ser
            115                 120

<210> SEQ ID NO 57
<211> LENGTH: 13
<212> TYPE: PRT
<213> ORGANISM: Homo sapiens

<400> SEQUENCE: 57

Ala Arg Val His Ala Ala Leu Tyr Tyr Gly Met Asp Val
 1               5                  10

<210> SEQ ID NO 58
<211> LENGTH: 120
<212> TYPE: PRT
<213> ORGANISM: Homo sapiens

<400> SEQUENCE: 58

Glu Val Gln Leu Val Gln Ser Gly Gly Glu Val Lys Lys Pro Gly Ala
 1               5                  10                  15

Ser Val Lys Val Ser Cys Lys Ala Ser Gly Tyr Thr Leu Ser Ser His
                20                  25                  30

Gly Ile Thr Trp Val Arg Gln Ala Pro Gly Gln Gly Leu Glu Trp Met
             35                  40                  45

Gly Trp Ile Ser Ala His Ser Gly His Ala Ser Asn Ala Gln Lys Val
 50                  55                  60

Glu Asp Arg Val Thr Met Thr Thr Asp Thr Ser Thr Asn Thr Ala Tyr
 65                  70                  75                  80

Met Glu Leu Arg Ser Leu Thr Ala Asp Thr Ala Val Tyr Tyr Cys
                 85                  90                  95

Ala Arg Val His Ala Ala Leu Tyr Tyr Gly Met Asp Val Trp Gly Gln
            100                 105                 110

Gly Thr Leu Val Thr Val Ser Ser
            115                 120

<210> SEQ ID NO 59
<211> LENGTH: 360
<212> TYPE: DNA
<213> ORGANISM: Homo sapiens

<400> SEQUENCE: 59
gaggtgcagc tggtgcagtc tggggctgag gtgaagaagc ctgggtcctc ggtgaaggtc      60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggaca gtccacgag cacagcctac     240 atggagctga gcagcctgag atctgaggac acggcggtgt actactgcgc tagaggcaga    300
cagatgttcg gtgcaggcat cgatttctgg ggccagggca ccctggtcac cgtctcctca    360
```

```
<210> SEQ ID NO 60
<211> LENGTH: 360
<212> TYPE: DNA
<213> ORGANISM: Homo sapiens

<400> SEQUENCE: 60
caggtgcagc tggtgcagtc tggggctgag gtgaagaagc ctgggtcctc ggtgaaggtc      60
tcctgcaagg cttctggagg caccttcagc cgttcggcta tcagctgggt gcgacaggcc     120
cctggacaag ggcttgagtg gatgggagtt atcatccctg cgtttggtga ggcaaactac     180
gcacagaagt tccagggcag agtcacgatt accgcggacg aatccacgag cacagcctac     240
atggagctga gcagcctgag atctgaggac acggcggtgt actactgcgc tagaggcaga     300
cagatgttcg gtgcaggcat cgatttctgg ggccagggca ccctggtcac cgtctcctca     360

<210> SEQ ID NO 61
<211> LENGTH: 360
<212> TYPE: DNA
<213> ORGANISM: Homo sapiens

<400> SEQUENCE: 61
caggtgcagc tggtgcagtc tggggctgag gtgaagaagc ctgggtcctc ggtgaaggta      60
tcatgcaagg cttctggagg caccttcagc gggtatgcta tctcttgggt gcgacaggcc     120
cctggacaag ggcttgagtg gatgggagtt atcatccctg cttttggtac agcaaactac     180
gcacagaagt tccagggcag agtcacgatt accgcggacg aatccacgag cacagcctac     240
atggagctga gcagcctgag atctgaggac acggcggtgt actactgcgc cagaggcaga     300
cagatgttcg gtgcaggcat cgatttctgg ggccagggca ccctggtcac cgtctcctca     360

<210> SEQ ID NO 62
<211> LENGTH: 360
<212> TYPE: DNA
<213> ORGANISM: Homo sapiens

<400> SEQUENCE: 62
caggtgcagc tggtgcagtc tggggctgag gtgaagaagc ctgggtcctc ggtgaaggtc      60
tcctgcaagg cttctggagg caccttctgg aggtatgcta tcagctgggt gcgacaggcc     120
cctggacaag ggcttgagtg gatgggagtt atcatcccta tctggggtaa agcaaactac     180
gcacagaagt tccagggcag agtcacgatt accgcggacg aatccacgag cacagcctac     240
atggagctga gcagcctgag atctgaggac acggcggtgt actactgcgc cagaggcaga     300
cagatgttcg gtgcaggcat cgatttctgg ggccagggca ccctggtcac cgtctcctca     360

<210> SEQ ID NO 63
<211> LENGTH: 360
<212> TYPE: DNA
<213> ORGANISM: Homo sapiens

<400> SEQUENCE: 63
caggtgcagc tggtgcagtc tggggctgag gtgaagaagc ctgggtcctc ggtgaaggtc      60
tcctgcaagg cttctggagg caccttcggg agctatgcta tctcttgggt gcgacaggcc     120
cctggacaag ggcttgagtg gatgggaggg atctatcctg cttttggtac agcaaactac     180
gcacagaagt tccagggcag agtcacgatt accgcggacg aatccacgag cacagcctac     240
atggagctga gcagcctgag atctgaggac acggcggtgt actactgcgc tagaggcaga     300
```
cagatgttcg gtgcaggcat cgatttctgg ggccagggca ccctggtcac cgtctcctca    360

<210> SEQ ID NO 64
<211> LENGTH: 360
<212> TYPE: DNA
<213> ORGANISM: Homo sapiens

<400> SEQUENCE: 64
caggtgcagc tggtgcagtc tggggctgag gtgaagaagc ctgggtcctc ggtgaaggtc     60
tcctgcaagg cttctggagg caccttcggg acgtatgcta tcagctgggt gcgacaggcc    120
cctggacaag ggcttgagtg gatgggaggg atctatccta ggtttggtac agcaaactac    180
gcacagaagt tccagggcag agtcacgatt accgcggacg aatccacgag cacagcctac    240
atggagctga gcagcctgag atctgaggac acggcggtgt actactgcgc tagaggcaga    300
cagatgttcg gtgcaggcat cgatttctgg ggccagggca ccctggtcac cgtctcctca    360

<210> SEQ ID NO 65
<211> LENGTH: 360
<212> TYPE: DNA
<213> ORGANISM: Homo sapiens

<400> SEQUENCE: 65
caggtgcagc tggtgcagtc tggggctgag gtgaagaagc ctgggtcctc ggtgaaggtc     60
tcctgcaagg cttctggagg caccttcagc ccgaaggcta tcagctgggt gcgacaggcc    120
cctggacaag ggcttgagtg gatgggagtg atcatcccta tctttggtcc ggcaaactac    180
gcacagaagt tccagggcag agtcacgatt accgcggacg aatccacgag cacagcctac    240
atggagctga gcagcctgag atctgaggac acggcggtgt actactgcgc tagaggcaga    300
cagatgttcg gtgcaggcat cgatttctgg ggccagggca ccctggtcac cgtctcctca    360

<210> SEQ ID NO 66
<211> LENGTH: 360
<212> TYPE: DNA
<213> ORGANISM: Homo sapiens

<400> SEQUENCE: 66
gaggttcagc tggtgcagtc tggaggtgag gtgaagaagc ctggggcctc agtgaaggtc     60
tcctgcaagg cttctggtta caccettagc agccatggta tcacctgggt gcgacaggcc    120
cctggacaag ggcttgagtg gatgggatgg atcagcgctc acagtggtca cgcaagcaat    180
gcacagaagg tcgaggacag agtcaccatg accacagaca catccacgaa cacagcctac    240
atggagctga ggagcctgac agctgacgac acggcggtgt actactgcgc cagagtccat    300
gccgccttgt actacggtat ggacgtctgg gggcaaggga ccctggtcac cgtctcctca    360

<210> SEQ ID NO 67
<211> LENGTH: 360
<212> TYPE: DNA
<213> ORGANISM: Homo sapiens

<400> SEQUENCE: 67
gaggttcagc tggtgcagtc tggaggtgag gtgaagaagc ctggggcctc agtgaaggtc     60
tcctgcaagg cttctggtta caccettagc agccatggta tcacctgggt gcgacaggcc    120
cctggacaag ggcttgagtg gatgggatgg atcagcgctc acagtggtca cgcaagcaat    180
gcacagaagg tcgaggacag agtcaccatg accacagaca catccacgaa cacagcctac    240
atggagctga ggagcctgac agctgacgac acggcggtgt actactgcgc cagagtccat    300

```
gccgccttgt accacggtat ggacgtctgg gggcaaggga ccctggtcac cgtctcctca    360
```

<210> SEQ ID NO 68
<211> LENGTH: 360
<212> TYPE: DNA
<213> ORGANISM: Homo sapiens

<400> SEQUENCE: 68

```
gaggttcagc tggtgcagtc tggaggtgag gtgaagaagc ctggggcctc agtgaaggtc     60
tcctgcaagg cttctggtta caccctttagc agccatggta tcacctgggt gcgacaggcc   120
cctggacaag gcttgagtg gatgggatgg atcagcgctc acagtggtca cgcaagcaat    180
gcacagaagg tcgaggacag agtcaccatg accacagaca catccacgaa cacagcctac    240
atggagctga ggagcctgac agctgacgac acggcggtgt actactgcgc cagagtgtgg    300
agggccttgt accacggtat ggacgtctgg gggcaaggga ccctggtcac cgtctcctca    360
```

<210> SEQ ID NO 69
<211> LENGTH: 336
<212> TYPE: DNA
<213> ORGANISM: Homo sapiens

<400> SEQUENCE: 69

```
aattttatgc tgactcagcc ccactctgtg tcggagtctc cggggaagac ggtaaccatc     60
tcctgcaccc gcagcagtgg cagcattgac agcaactatg tgcagtggta ccagcagcgc   120
ccgggcagtg cccccaccac tgtgatctat gaggataacc aaagaccctc tggggtccct    180
gatcggttct ctggctccat cgacagctcc tccaactctg cctccctcac catctctgga    240
ctgaagactg aggacgaggc tgactactac tgtcagtctt atgatagcaa caataggcat    300
gtgatattcg gcggagggac caagctgacc gtccta                              336
```

<210> SEQ ID NO 70
<211> LENGTH: 324
<212> TYPE: DNA
<213> ORGANISM: Homo sapiens

<400> SEQUENCE: 70

```
ttgtctgtgc tgactcagcc accctcagtg tcagtggccc caggacagac ggccaggatt     60
acctgtgggg gaaacaacat tggaagtaaa ggtgtgcact ggtaccagca gaagccaggc   120
caggcccctg tgctggtcgt ctatgatgat agcgaccggc cctcagggat ccctgagcga    180
ttctctggct ccaactctgg gaacacggcc accctgacca tcagcagggt cgaagccggg    240
gatgaggccg actattactg tcaggtgtgg gacagtagta gtgatcattg ggtgttcggc    300
ggagggacca agctgaccgt ccta                                           324
```

<210> SEQ ID NO 71
<211> LENGTH: 120
<212> TYPE: PRT
<213> ORGANISM: Homo sapiens

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Gln Met Phe Gly Ala Gly Ile Asp Phe Trp Gly Gln
                100                 105                 110

Gly Thr Leu Val Thr Val Ser Ser
                115                 120

<210> SEQ ID NO 72
<211> LENGTH: 120
<212> TYPE: PRT
<213> ORGANISM: Homo sapiens

<400> SEQUENCE: 72

Glu Val Gln Leu Val Gln Ser Gly Gly Glu Val Lys Lys Pro Gly Ala
 1               5                  10                  15

Ser Val Lys Val Ser Cys Lys Ala Ser Gly Tyr Thr Leu Ser Ser His
                 20                  25                  30

Gly Ile Thr Trp Val Arg Gln Ala Pro Gly Gln Gly Leu Glu Trp Met
             35                  40                  45

Gly Trp Ile Ser Ala His Ser Gly His Ala Ser Asn Ala Gln Lys Val
         50                  55                  60

Glu Asp Arg Val Thr Met Thr Thr Asp Thr Ser Thr Asn Thr Ala Tyr
 65                  70                  75                  80

Met Glu Leu Arg Ser Leu Thr Ala Asp Thr Ala Val Tyr Tyr Cys
                 85                  90                  95

Ala Arg Val His Ala Ala Leu Tyr Tyr Gly Met Asp Val Trp Gly Gln
                100                 105                 110

Gly Thr Leu Val Thr Val Ser Ser
                115                 120

<210> SEQ ID NO 73
<211> LENGTH: 451
<212> TYPE: PRT
<213> ORGANISM: Homo sapiens

<400> SEQUENCE: 73

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
                 20                  25                  30

Trp Met Ser Trp Val Arg Gln Ala Pro Gly Lys Gly Leu Glu Trp Val
             35                  40                  45

Ala Asn Ile Lys Gln Asp Gly Ser Glu Lys Tyr Tyr Val Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Gly Trp Phe Gly Glu Leu Ala Phe Asp Tyr Trp Gly
                100                 105                 110

Gln Gly Thr Leu Val Thr Val Ser Ser Ala Ser Thr Lys Gly Pro Ser
             115                 120                 125

```
Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 74
<211> LENGTH: 215
<212> TYPE: PRT
<213> ORGANISM: Homo sapiens

<400> SEQUENCE: 74

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
```

```
            35                  40                  45
Ile Tyr Asp Ala Ser Ser Arg Ala Thr Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Leu Pro
                 85                  90                  95
Trp Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 75
<211> LENGTH: 11
<212> TYPE: PRT
<213> ORGANISM: Homo sapiens

<400> SEQUENCE: 75

Gln Ser Tyr Asp Ser Asn Leu Arg His Val Ile
 1               5                  10

<210> SEQ ID NO 76
<211> LENGTH: 11
<212> TYPE: PRT
<213> ORGANISM: Homo sapiens

<400> SEQUENCE: 76

Gln Ser Tyr Asp Ser Asn Ile Arg His Val Ile
 1               5                  10

<210> SEQ ID NO 77
<211> LENGTH: 34
<212> TYPE: PRT
<213> ORGANISM: Homo sapiens

<400> SEQUENCE: 77

Gly Val Pro Asp Arg Phe Ser Gly Ser Ile Asp Ser Ser Asn Trp
 1               5                  10                  15

Ala Ser Leu Thr Ile Ser Gly Leu Lys Thr Glu Asp Glu Ala Asp Tyr
            20                  25                  30

Tyr Cys

<210> SEQ ID NO 78
<211> LENGTH: 34
<212> TYPE: PRT
<213> ORGANISM: Homo sapiens
```

```
<400> SEQUENCE: 78

Gly Val Pro Asp Arg Phe Ser Gly Ser Ile Asp Ser Ser Ser Asn Val
1               5                   10                  15

Ala Ser Leu Thr Ile Ser Gly Leu Lys Thr Glu Asp Glu Ala Asp Tyr
            20                  25                  30

Tyr Cys
```